United States Patent
Tsai et al.

(10) Patent No.: US 10,851,337 B2
(45) Date of Patent: Dec. 1, 2020

(54) 3D POLYMERIC INSERT TO APPLY UNIFORM ELECTRIC FIELD IN CIRCULAR CULTUREWARE

(71) Applicant: OKINAWA INSTITUTE OF SCIENCE AND TECHNOLOGY SCHOOL CORPORATION, Okinawa (JP)

(72) Inventors: Hsieh-Fu Tsai, Okinawa (JP); Amy Shen Fried, Okinawa (JP); Ji-Yen Cheng, Taipei (TW)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 249 days.

(21) Appl. No.: 15/759,734

(22) PCT Filed: Sep. 16, 2016

(86) PCT No.: PCT/JP2016/004255
§ 371 (c)(1),
(2) Date: Mar. 13, 2018

(87) PCT Pub. No.: WO2017/047098
PCT Pub. Date: Mar. 23, 2017

(65) Prior Publication Data
US 2018/0251717 A1   Sep. 6, 2018

Related U.S. Application Data

(60) Provisional application No. 62/220,841, filed on Sep. 18, 2015.

(51) Int. Cl.
*C12M 1/42* (2006.01)
*C12M 1/22* (2006.01)
*C12M 1/00* (2006.01)

(52) U.S. Cl.
CPC .......... *C12M 35/02* (2013.01); *C12M 23/02* (2013.01); *C12M 23/10* (2013.01)

(58) Field of Classification Search
CPC ......... C12M 35/02; C12M 1/22; C12M 23/10
(Continued)

(56) References Cited

U.S. PATENT DOCUMENTS

| 3,661,746 A | 5/1972 | Lucas |
| 4,804,450 A | 2/1989 | Mochizuki et al. |

(Continued)

FOREIGN PATENT DOCUMENTS

| WO | 2008/088240 A2 | 7/2008 |
| WO | 2013/167185 A1 | 11/2013 |

OTHER PUBLICATIONS

Huang, Y.-J., Samorajski, J., Kreimer, R. & Searson, P. C. The Influence of Electric Field and Confinement on Cell Motility. PLoS ONE 8, e59447 (2013). (Mentioned in paragraph No. 8 of the as-filed specification.).

(Continued)

*Primary Examiner* — Holly Kipouros
(74) *Attorney, Agent, or Firm* — Westerman, Hattori, Daniels & Adrian, LLP

(57) ABSTRACT

A disclosed insert for a circular-shaped petri dish can generate a substantially uniform electric field across the petri dish that is filled with a fluid establishing a salt bridge. The insert includes a circular-shaped bottom plate defining a circular-shaped space; a side channel vertically erecting from a circular periphery of said bottom plate; and a pair of current rectifying chambers each having a generally planar shape communicating with the side channel. In at least some aspects of the invention, portions of the side channel bridging the pair of current rectifying chambers each have a generally concave top profile having a lowest point at the (Continued)

center between the pair of current rectifying chambers such that, when the salt bridge is established, the circular-shaped space defined by the bottom plate exhibits a substantially uniform electric field in a substantially entire area of the space.

5 Claims, 11 Drawing Sheets

(58) Field of Classification Search
USPC .................................................. 435/305, 100
See application file for complete search history.

(56) References Cited

U.S. PATENT DOCUMENTS

| | | |
|---|---|---|
| 4,948,089 A | 8/1990 | Knodel et al. |
| 5,011,586 A | 4/1991 | Finney et al. |
| 5,134,070 A | 7/1992 | Casnig |
| 5,717,371 A | 2/1998 | Crow |
| 6,686,193 B2 | 2/2004 | Maher et al. |
| 7,824,901 B2 | 11/2010 | Walters |
| 2013/0260434 A1 | 10/2013 | Mueller-Hartmann et al. |
| 2014/0186941 A1 | 7/2014 | Zhou et al. |

OTHER PUBLICATIONS

Tandon, N. et al. Electrical stimulation systems for cardiac tissue engineering. Nat. Protocols 4, 155-173 (2009). (Mentioned in paragraph Nos. 8 and 67 of the as-filed specification.).

Babona-Pilipos, R., Droujinine, I. A., Popovic, M. R. & Morshead, C. M. Adult subependymal neural precursors, but not differentiated cells, undergo rapid cathodal migration in the presence of direct current electric fields. PLoS ONE 6, e23808 (2011). (Mentioned in paragraph Nos. 8 and 67 of the as-filed specification.).

McDonough, P. M. & Glembotski, C. C. Induction of atrial natriuretic factor and myosin light chain-2 gene expression in cultured ventricular myocytes by electrical stimulation of contraction. J. Biol. Chem. 267, 11665-11668 (1992). (Mentioned in paragraph Nos. 8 and 67 of the as-filed specification.).

Radisic, M. et al. Functional assembly of engineered myocardium by electrical stimulation of cardiac myocytes cultured on scaffolds. Proc. Natl. Acad. Sci. U.S.A. 101, 18129-18134 (2004). (Mentioned in paragraph Nos. 8 and 67 of the as-filed specification.).

Serena, E. et al. Electrical stimulation of human embryonic stem cells: Cardiac differentiation and the generation of reactive oxygen species. Experimental Cell Research 315, 3611-3619 (2009). (Mentioned in paragraph Nos. 8 and 67 of the as-filed specification.).

Barash, Y. et al. Electric Field Stimulation Integrated into Perfusion Bioreactor for Cardiac Tissue Engineering. Tissue Engineering Part C: Methods 16, 1417-1426 (2010). (Mentioned in paragraph Nos. 8 and 67 of the as-filed specification.).

Hronik-Tupaj, M., Rice, W. L., Cronin-Golomb, M., Kaplan, D. L. & Georgakoudi, I. Osteoblastic differentiation and stress response of human mesenchymal stem cells exposed to alternating current electric fields. BioMedical Engineering OnLine 10, 9 (2011). (Mentioned in paragraph Nos. 8 and 67 of the as-filed specification.).

Marotta, M., Bragos, R. & Gomez-Foix, A. M. Design and performance of an electrical stimulator for long-term contraction of cultured muscle cells. BioTechniques 36, 68-73 (2004). (Mentioned in paragraph No. 8 of the as-filed specification.).

International Search Report (ISR) issued in PCT/JP2016/004255 dated Dec. 2016.

Written Opinion (PCT/ISA/237) issued in PCT/JP2016/004255 dated Dec. 2016.

Tsai, Hsieh-Fu et al., "Evaluation of EGFR and RTK Signaling in the Electrotaxis of Lung Adenocarcinoma Cell sunder Direct-Current Electric Field Stimulation", Plos ONE, Aug. 2013, vol. 8, No. 8, e73418, p. 1-20, ISSN 1932-6203 (Cited in the ISR.).

Garcia-Sanchez, Tomas et al., "Design and Implementation of a Microelectrode Assembly for Use on Noncontact In Situ Electroporation of Adherent Cells", J. Membrane Biol., 2012, vol. 245, No. 10, p. 617-624, ISSN 1432-1424 (Cited in the ISR.).

Tsai, Hsieh-Fu et al., "Uniform electric field generation in circular multi-well culture plates using polymeric inserts", Sci. Rep., May 2016, vol. 6, 26222, p. 1-11, ISSN 2045-2322 (Cited in the ISR.).

Huang, Ching-Wen et al., "Gene Expression of Human Lung Cancer Cell Line CL1-5in Response to a Direct Current Electric Field", PLoS ONE, 2011, vol. 6, No. 10, e25928, p. 1-13, ISSN 1932-6203 (Cited in the ISR.).

Gross et al., "Optical imaging of cell membrane potential changes induced by applied electric fields", Biophysical Journal, vol. 50, Aug. 1986, pp. 339-348.

Jen et al., "A handheld pre-concentrator for the rapid collection of cancerous cells using di-electrophoresis generated by circular microelectrodes in stepping electric fields", Biomicrofluidics 5, 034101 (2011).

Shilpee et al., "Vertical electric field stimulated neural cell functionality on porous amorphous carbon electrodes", Biomaterials 34 (2013) 9252-9263.

Shen, A., "Getting the most from microfluidic platforms for biomedical applications (Conference Presentation)", Progress in Biomedical Optics and Imaging, SPIE—International Society For Optical Engineering, Mar. 24, 2016, vol. 9705; pp. 970510-970510; cited in Extended (supplementary) European Search Report dated Sep. 6, 2018.

Shen, A., "Getting the most from microfluidic platforms for biomedical applications (Conference Presentation)", SPIE Digital Library, Apr. 26, 2016, pp. 1-1; cited in Extended (supplementary) European Search Report dated Sep. 6, 2018.

Extended (supplementary) European Search Report dated Sep. 6, 2018, issued in counterpart European Application No. 16845972.5. (5 pages).

McCaig, C. D., Song, B. & Rajnicek, A. M. Electrical dimensions in cell science. J Cell Sci 122, 4267-4276 (2009). (Mentioned in paragraph Nos. 2 and 8 of the as-filed specification.).

McCaig, C. D. Electric fields, contact guidance and the direction of nerve growth. J Embryol Exp Morphol 94, 245-255 (1986). (Mentioned in paragraph Nos. 2 and 8 of the as-filed specification.).

Messerli, M. A. & Graham, D. M. Extracellular Electrical Fields Direct Wound Healing and Regeneration. Biol Bull 221, 79-92 (2011). (Mentioned in paragraph Nos. 2 and 8 of the as-filed specification.).

Levin, M. Morphogenetic fields in embryogenesis, regeneration, and cancer: Non-local control of complex patterning. Biosystems 109, 243-261 (2012). (Mentioned in paragraph Nos. 2 and 8 of the as-filed specification.).

Golberg, A. et al. Skin Rejuvenation with Non-Invasive Pulsed Electric Fields. Scientific Reports 5, 10187 (2015). (Mentioned in paragraph Nos. 2 and 8 of the as-filed specification.).

Giugni, T. D., Braslau, D. L. & Haigler, H. T. Electric field-induced redistribution and postfield relaxation of epidermal growth factor receptors on A431 cells. J Cell Biol 104, 1291-1297 (1987). (Mentioned in paragraph Nos. 3 and 8 of the as-filed specification.).

Rochlin, M. W. & Peng, H. B. Localization of intracellular proteins at acetylcholine receptor clusters induced by electric fields in Xenopus muscle cells. J Cell Sci 94, 73-83 (1989). (Mentioned in paragraph Nos. 3 and 8 of the as-filed specification.).

McBain, V. A., Forrester, J. V. & McCaig, C. D. HGF, MAPK, and a Small Physiological Electric Field Interact during Corneal Epithelial Cell Migration. Investigative Opthalmology & Visual Science 44, 540 (2003). (Mentioned in paragraph Nos. 3 and 8 of the as-filed specification.).

Zhao, M., Bai, H., Wang, E., Forrester, J. V. & McCaig, C. D. Electrical stimulation directly induces pre-angiogenic responses in vascular endothelial cells by signaling through VEGF receptors. J Cell Sci 117, 397-405 (2004). (Mentioned in paragraph Nos. 3 and 8 of the as-filed specification.).

Zhang, H. L. & Peng, H. B. Mechanism of Acetylcholine Receptor Cluster Formation Induced by DC Electric Field. PLoS ONE 6, e26805 (2011). (Mentioned in paragraph Nos. 3 and 8 of the as-filed specification.).

(56) References Cited

OTHER PUBLICATIONS

Djamgoz, M. B. A., Mycielska, M., Madeja, Z., Fraser, S. P. & Korohoda, W. Directional movement of rat prostate cancer cells in direct-current electric field involvement of voltage-gated Na+ channel activity. J Cell Sci 114, 2697-2705 (2001). (Mentioned in paragraph Nos. 3 and 8 of the as-filed specification.).
Li, L. et al. Direct-Current Electrical Field Guides Neuronal Stem/Progenitor Cell Migration. Stem Cells 26, 2193-2200 (2008). (Mentioned in paragraph Nos. 3 and 8 of the as-filed specification.).
Ozkucur, N., Monsees, T. K., Perike, S., Do, H. Q. & Funk, R. H. W. Local Calcium Elevation and Cell Elongation Initiate Guided Motility in Electrically Stimulated Osteoblast-Like Cells. PLoS ONE 4, e6131 (2009). (Mentioned in paragraph Nos. 3 and 8 of the as-filed specification.).
Ozkucur, N., Perike, S., Sharma, P. & Funk, R. H. Persistent directional cell migration requires ion transport proteins as direction sensors and membrane potential differences in order to maintain directedness. BMC Cell Biology 12, 4 (2011). (Mentioned in paragraph Nos. 3 and 8 of the as-filed specification.).
Perike, S. et al. Phospho-NHE3 forms membrane patches and interacts with beta-actin to sense and maintain constant direction during cell migration. Experimental Cell Research 324, 13-29 (2014). (Mentioned in paragraph Nos. 3 and 8 of the as-filed specification.).
McCaig, C. D. & Dover, P. J. Raised Cyclic-AMP and a Small Applied Electric Field Influence Differentiation, Shape, and Orientation of Single Myoblasts. Developmental Biology 158, 172-182 (1993). (Mentioned in paragraph Nos. 3 and 8 of the as-filed specification.).
Trollinger, D. R., Rivkah Isseroff, R. & Nuccitelli, R. Calcium Channel Blockers Inhibit Galvanotaxis in Human Keratinocytes. J. Cell. Physiol. 193, 1-9 (2002). (Mentioned in paragraph Nos. 3 and 8 of the as-filed specification.).
Zhao, M. et al. Electrical signals control wound healing through phosphatidylinositol-3-OH kinase-gamma and PTEN. Nature 442, 457-460 (2006). (Mentioned in paragraph Nos. 3 and 8 of the as-filed specification.).
Wartenberg, M. et al. Direct Current Electrical Fields Induce Apoptosis in Oral Mucosa Cancer Cells by NADPH Oxidase-Derived Reactive Oxygen Species. Bioelectromagnetics 29, 47-54 (2008). (Mentioned in paragraph Nos. 3 and 8 of the as-filed specification.).
Li, F. et al. Superoxide plays critical roles in electrotaxis of fibrosarcoma cells via activation of ERK and reorganization of the cytoskeleton. Free Radical Biology and Medicine 52, 1888-1896 (2012). (Mentioned in paragraph Nos. 3 and 8 of the as-filed specification.).
Guo, X. et al. The Galvanotactic Migration of Keratinocytes is Enhanced by Hypoxic Preconditioning. Scientific Reports 5, 10289 (2015). (Mentioned in paragraph Nos. 3 and 8 of the as-filed specification.).
Kao, Y.-C. et al. Modulating chemotaxis of lung cancer cells by using electric fields in a microfluidic device. Biomicrofluidics 8, 024107 (2014). (Mentioned in paragraph Nos. 4 and 8 of the as-filed specification.).
Song, S., Han, H., Ko, U. H., Kim, J. & Shin, J. H. Collaborative effects of electric field and fluid shear stress on fibroblast migration. Lab Chip 13, 1602-1611 (2013). (Mentioned in paragraph Nos. 4 and 8 of the as-filed specification.).
Boyden, S. The Chemotactic Effect of Mixtures of Antibody and Antigen on Polymorphonuclear Leucocytes. J Exp Med 115, 453-466 (1962). (Mentioned in paragraph Nos. 4 and 8 of the as-filed specification.).
Erickson, C. A. & Nuccitelli, R. Embryonic fibroblast motility and orientation can be influenced by physiological electric fields. J Cell Biol 98, 296-307 (1984). (Mentioned in paragraph Nos. 5, 8, and 25 of the as-filed specification.).

Zhao, M., Agius-Fernandez, A., Forrester, J. V. & McCaig, C. D. Orientation and directed migration of cultured corneal epithelial cells in small electric fields are serum dependent. J Cell Sci 109, 1405-1414 (1996). (Mentioned in paragraph Nos. 5 and 8 of the as-filed specification.).
Song, B. et al. Application of direct current electric fields to cells and tissues in vitro and modulation of wound electric field in vivo. Nat. Protocols 2, 1479-1489 (2007). (Mentioned in paragraph Nos. 5 and 8 of the as-filed specification.).
Huang, C.-W., Cheng, J.-Y., Yen, M.-H. & Young, T.-H. Electrotaxis of lung cancer cells in a multiple-electric-field chip. Biosensors and Bioelectronics 24, 3510-3516 (2009). (Mentioned in paragraph Nos. 5, 8, 17, and 25 of the as-filed specification.).
Huang, C.-W. et al. Gene Expression of Human Lung Cancer Cell Line CL1-5 in Response to a Direct Current Electric Field. PLoS ONE 6, e25928 (2011). (Mentioned in paragraph Nos. 5-6, 8, and 36 of the as-filed specification.).
Tsai, H.-F. et al. Evaluation of EGFR and RTK Signaling in the Electrotaxis of Lung Adenocarcinoma Cells under Direct-Current Electric Field Stimulation. PLoS ONE 8, e73418 (2013). (Mentioned in paragraph Nos. 5-6, 8, 17, 25, 36, and 48 of the as-filed specification.).
Marotta, M., Bragos, R. & Gomez-Foix, A. M. Design and performance of an electrical stimulator for long-term contraction of cultured muscle cells. BioTechniques 36, 68-73 (2004). (Mentioned in paragraph Nos. 6 and 8 of the as-filed specification.).
Genovese, J. A. et al. Electrostimulation induces cardiomyocyte predifferentiation of fibroblasts. Biochemical and Biophysical Research Communications 370, 450-455 (2008). (Mentioned in paragraph Nos. 6 and 8 of the as-filed specification.).
Okutsu, S., Hatakeyama, H., Kanazaki, M., Tsubokawa, H. & Nagatomi, R. Electric Pulse Stimulation Induces NMDA Glutamate Receptor mRNA in NIH3t3 Mouse Fibroblasts. The Tohoku Journal of Experimental Medicine 215, 181-187 (2008). (Mentioned in paragraph Nos. 6 and 8 of the as-filed specification.).
Yamasaki, K.-i. et al. Control of myotube contraction using electrical pulse stimulation for bio-actuator. Journal of Artificial Organs 12, 131-137 (2009). (Mentioned in paragraph Nos. 6 and 8 of the as-filed specification.).
Burch, N. et al. Electric Pulse Stimulation of Cultured Murine Muscle Cells Reproduces Gene Expression Changes of Trained Mouse Muscle. PLoS ONE 5, e10970 (2010). (Mentioned in paragraph Nos. 6 and 8 of the as-filed specification.).
Lin, F. et al. Lymphocyte Electrotaxis In Vitro and In Vivo. J Immunol 181, 2465-2471 (2008). (Mentioned in paragraph Nos. 6 and 8 of the as-filed specification.).
Garcia-Sanchez, T. et al. Design and Implementation of a Microelectrode Assembly for Use on Noncontact In Situ Electroporation of Adherent Cells. J Membrane Biol 245, 617-624 (2012). (Mentioned in paragraph Nos. 6 and 8 of the as-filed specification.).
Ahirwar, D. K. et al. Non-contact method for directing electrotaxis. Scientific Reports 5, 11005 (2015). (Mentioned in paragraph Nos. 6 and 8 of the as-filed specification.).
Sachs, E., Cima, M., Williams, P., Brancazio, D. & Cornie, J. Three Dimensional Printing: Rapid Tooling and Prototypes Directly from a CAD Model. J. Eng. Ind 114, 481-488 (1992). (Mentioned in paragraph Nos. 7-8 of the as-filed specification.).
Waldbaur, A., Rapp, H., Lange, K & Rapp, B. E. Let there be chip-towards rapid prototyping of microfluidic devices: one-step manufacturing processes. Anal. Methods 3, 2681-2716 (2011). (Mentioned in paragraph Nos. 7-8 of the as-filed specification.).
Waldbaur, A., Cameiro, B., Hettich, P., Wilhelm, E. & Rapp, B. E. Computer-aided microfluidics (CAMF): from digital 3d-CAD models to physical structures within a day. Microfluid Nanofluid 15, 625-635 (2013). (Mentioned in paragraph Nos. 7-8 of the as-filed specification.).
Shallan, A. I., Smejkal, P., Corban, M., Guijt, R. M. & Breadmore, M. C. Cost-Effective Three-Dimensional Printing of Visibly Transparent Microchips within Minutes. Anal. Chem. 86, 3124-3130 (2014). (Mentioned in paragraph Nos. 7-8 of the as-filed specification.).

(56) References Cited

OTHER PUBLICATIONS

Ho, C. M. B., Ng, S. H., Li, K. H. H. & Yoon, Y.-J. 3d printed microfluidics for biological applications. Lab Chip 15, 3627-3637 (2015). (Mentioned in paragraph Nos. 7-8 of the as-filed specification.).

Tsai, H.-F., Peng, S.-W., Wu, C.-Y., Chang, H.-F. & Cheng, J.-Y. Electrotaxis of oral squamous cell carcinoma cells in a multiple-electric-field chip with uniform flow field. Biomicrofluidics 6, 34116 (2012). (Mentioned in paragraph Nos. 8, 17, and 25 of the as-filed specification.).

Hobbie, R. K. & Roth, B. J. Intermediate Physics for Medicine and Biology (Springer, 2015). (Mentioned in paragraph Nos. 8 and 19 of the as-filed specification. Mentioned in paragraph 56, described as NPL No. 60 of the as-filed specification.).

Larson, R. & Edwards, B. H. Calculus Multivariable (Cengage Learning, 2009). (Mentioned in paragraph Nos. 8 and 20 of the as-filed specification. Mentioned in paragraph 60, described as NPL No. 61 of the as-filed specification.).

Cheng, J.-Y., Wei, C.-W., Hsu, K-H. & Young, T.-H. Direct-write laser micromachining and universal surface modification of PMMA for device development. Sensors and Actuators B: Chemical 99, 186-196 (2004). (Mentioned in paragraph Nos. 8 and 24 of the as-filed specification.).

Cheng, J.-Y., Yen, M.-H., Kuo, C.-T. & Young, T.-H. A transparent cell-culture microchamber with a variably controlled concentration gradient generator and flow field rectifier. Biomicrofluidics 2, 24105 (2008). (Mentioned in paragraph Nos. 8 and 24 of the as-filed specification.).

Brown, M. J. & Loew, L. M. Electric field-directed fibroblast locomotion involves cell surface molecular reorganization and is calcium independent. J Cell Biol 127, 117-128 (1994). (Mentioned in paragraph Nos. 8 and 40 of the as-filed specification.).

Finkelstein, E. et al. Roles of microtubules, cell polarity and adhesion in electric-field-mediated motility of 3t3 fibroblasts. J Cell Sci 117, 1533-1545 (2004). (Mentioned in paragraph Nos. 8 and 40 of the as-filed specification.).

[Fig. 1(a)]
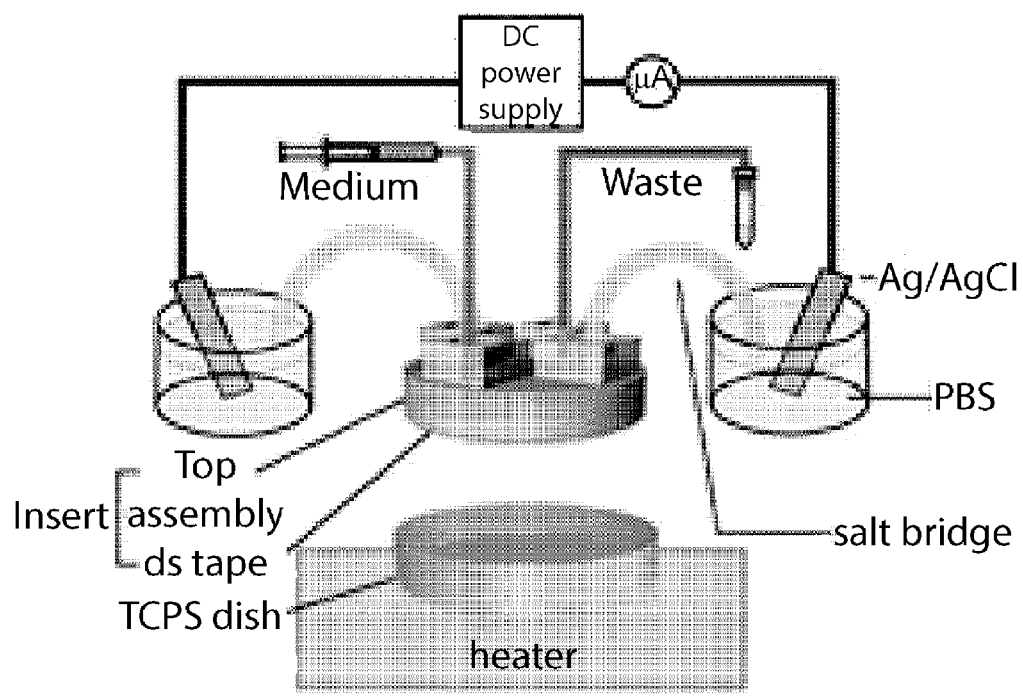
[Fig. 1(b)]
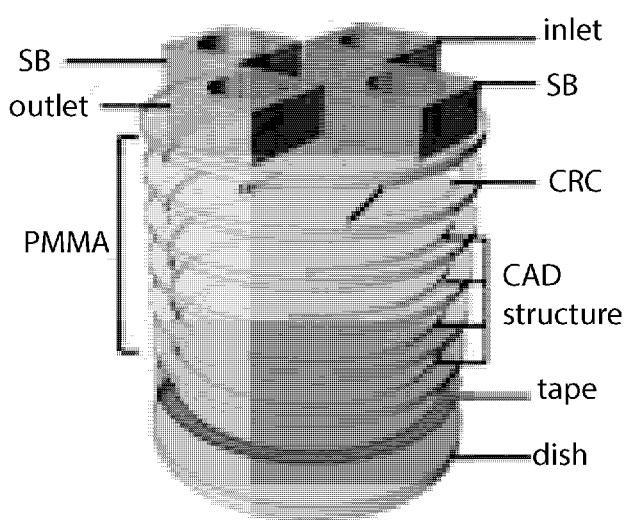

[Fig. 1(c)]
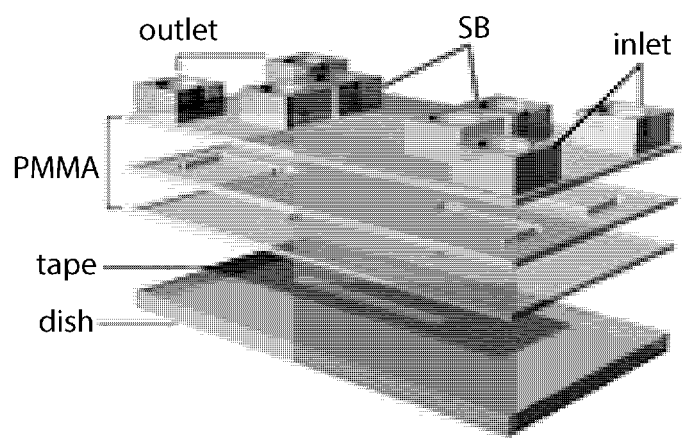

[Fig. 2(a)]
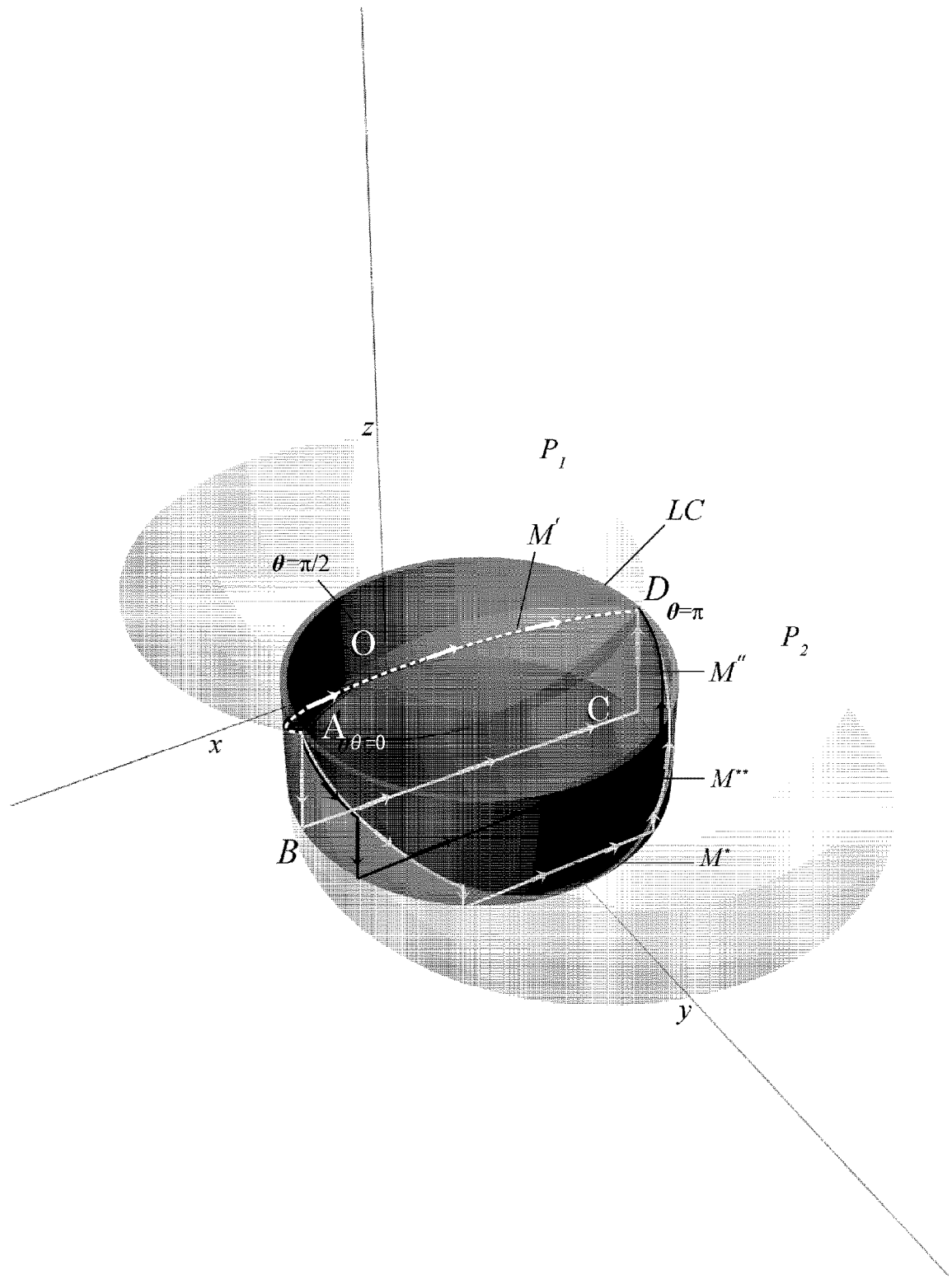

[Fig. 2(b)-(d)]
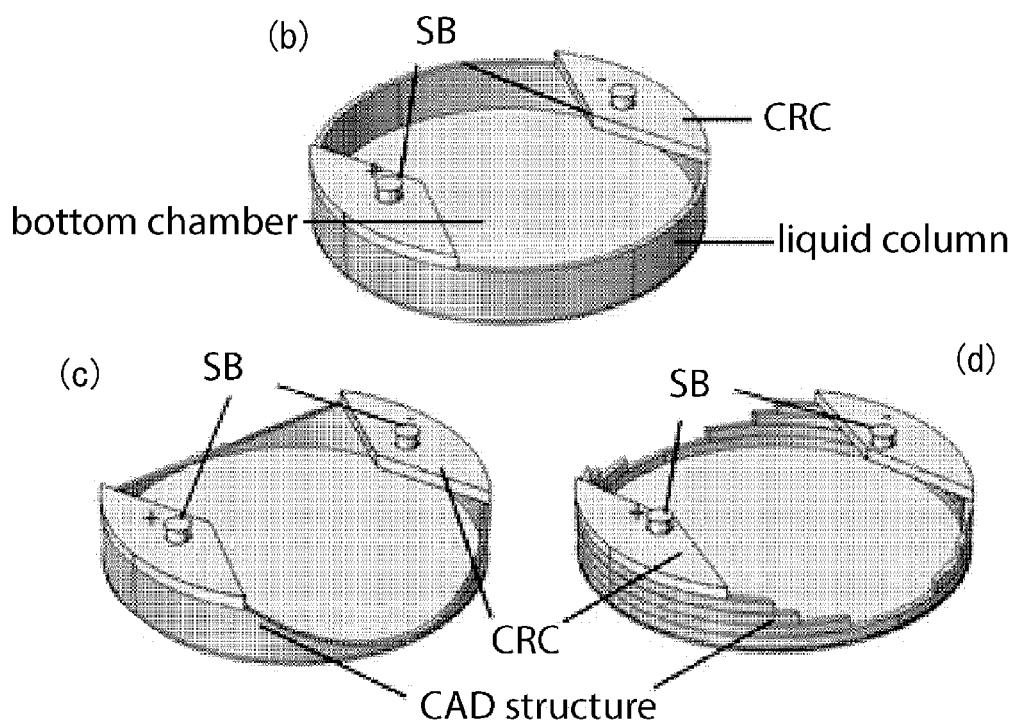

[Fig. 3]
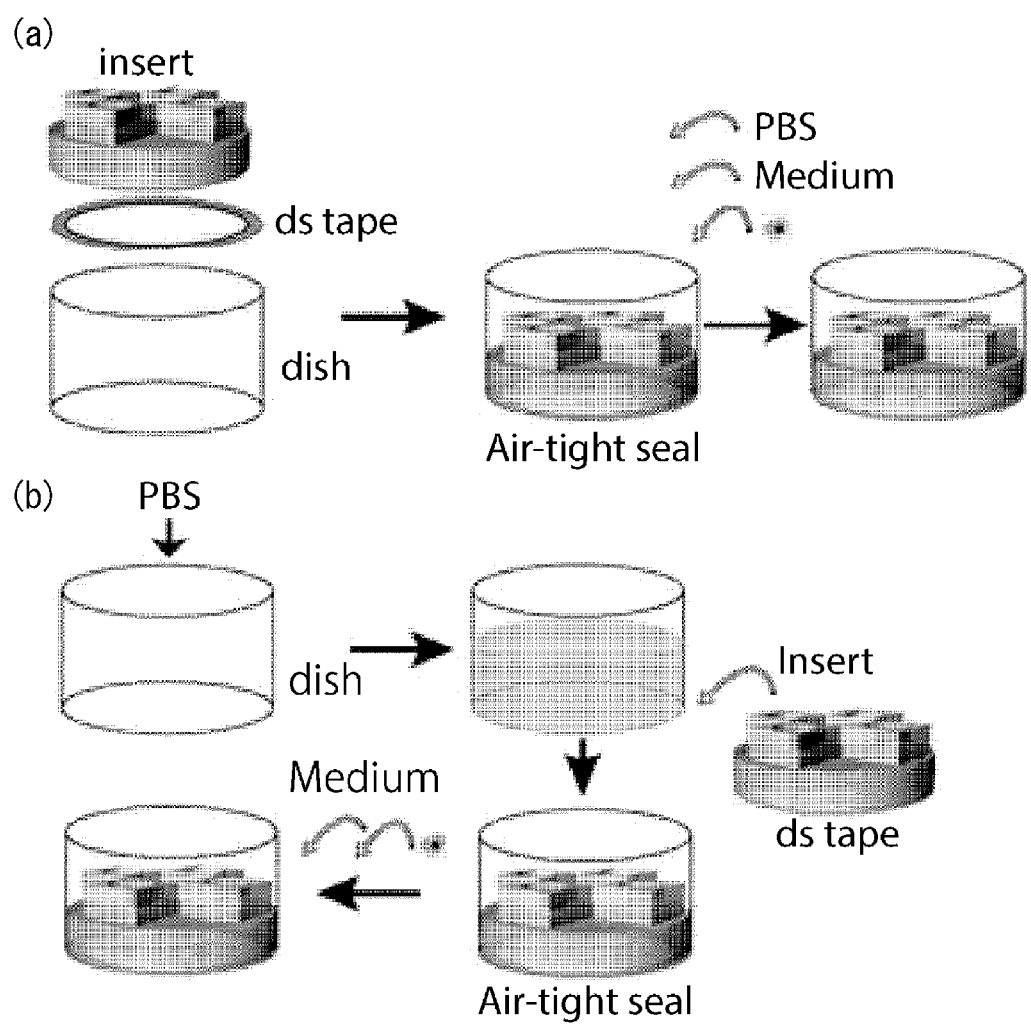

[Fig. 4]
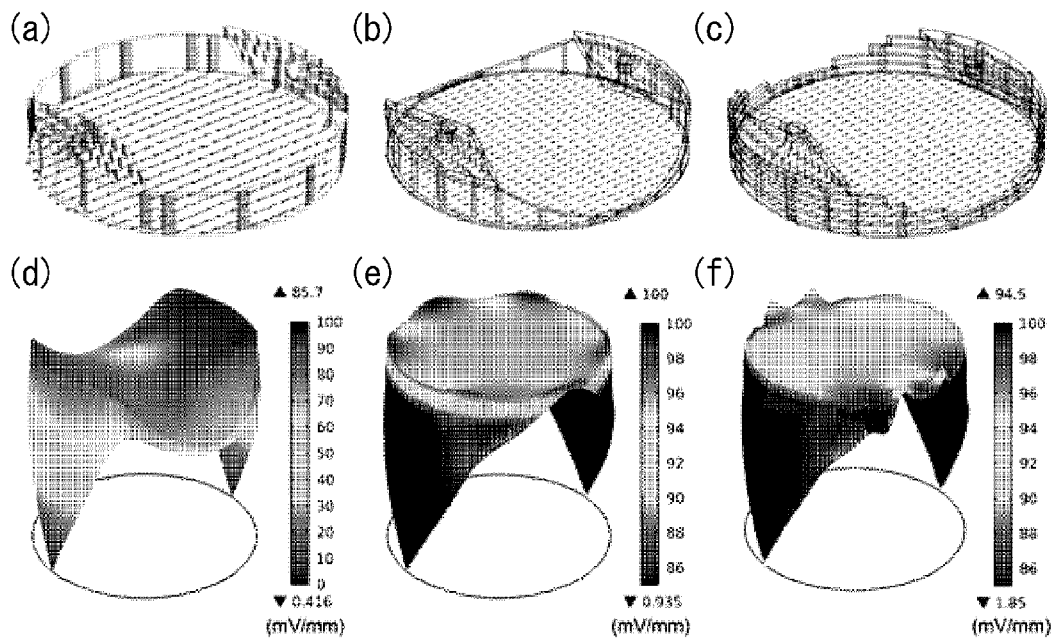
[Fig. 5]
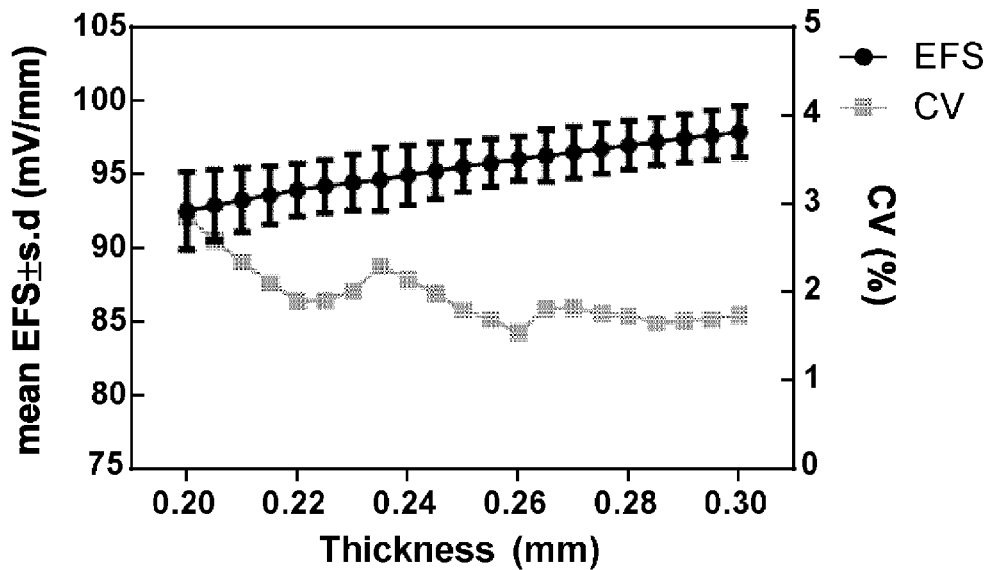

[Fig. 6]
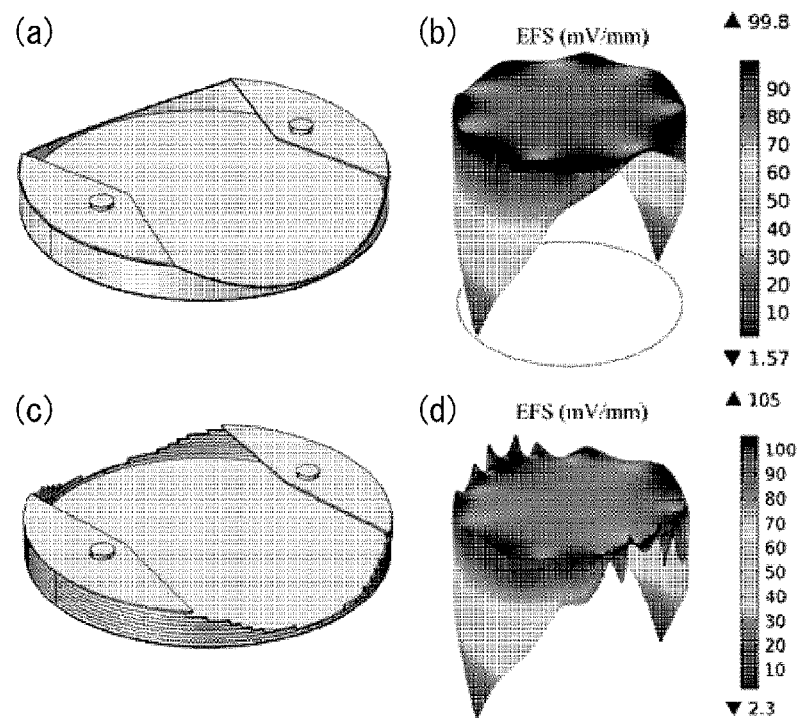
[Fig. 7]
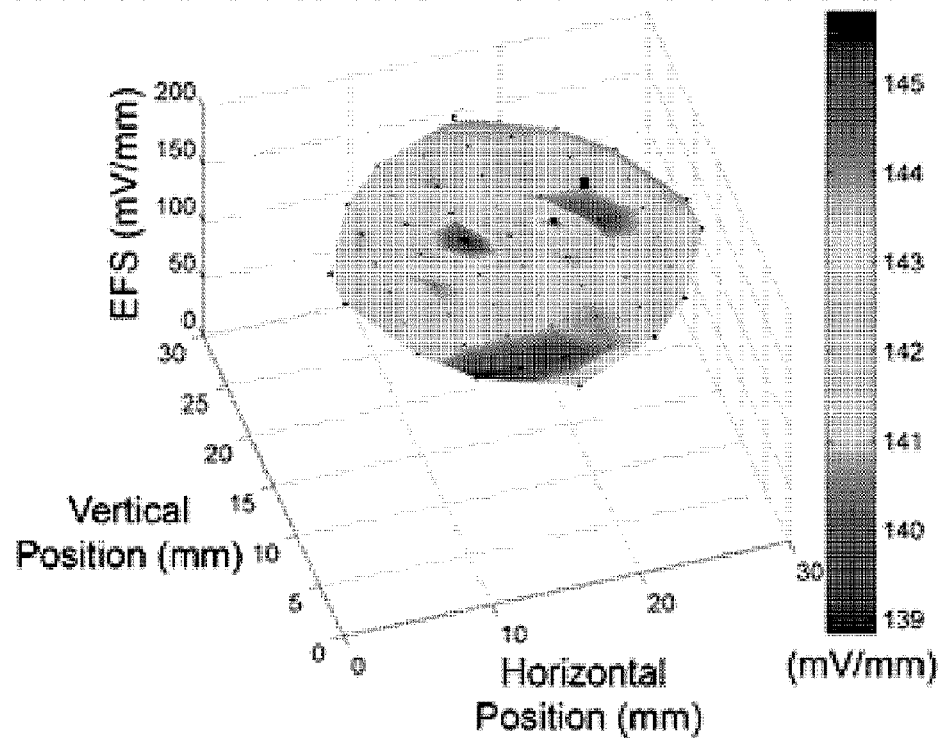

[Fig. 8]
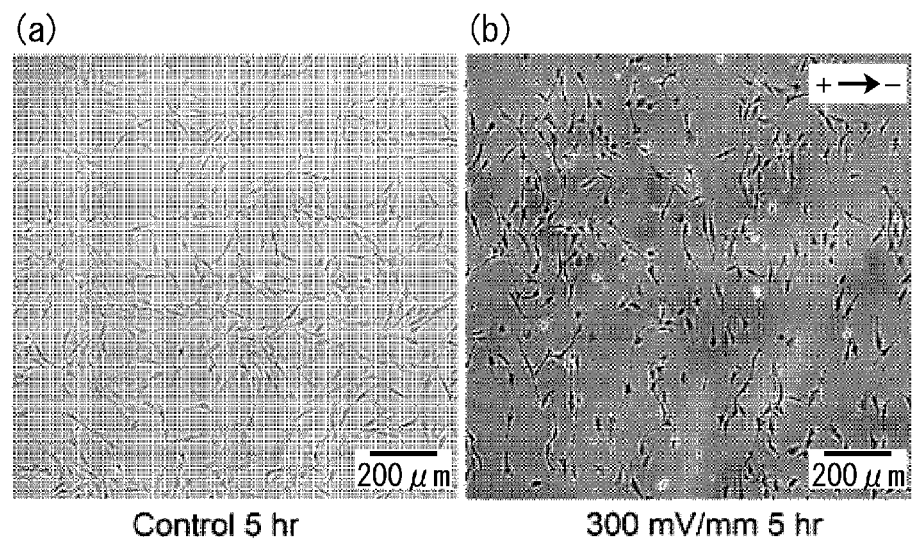
[Fig. 9(a)]
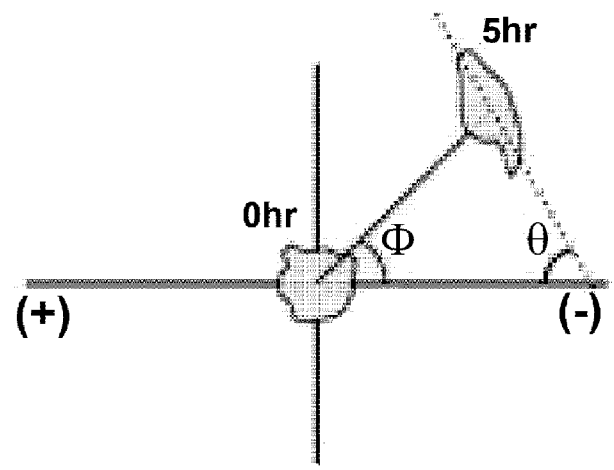
Directedness: $\sum_{i=1}^{n} \frac{\cos\Phi_i}{n}$
Orientation: $\sum_{i=1}^{n} \frac{\cos 2\theta_i}{n}$

[Fig. 9(b)]
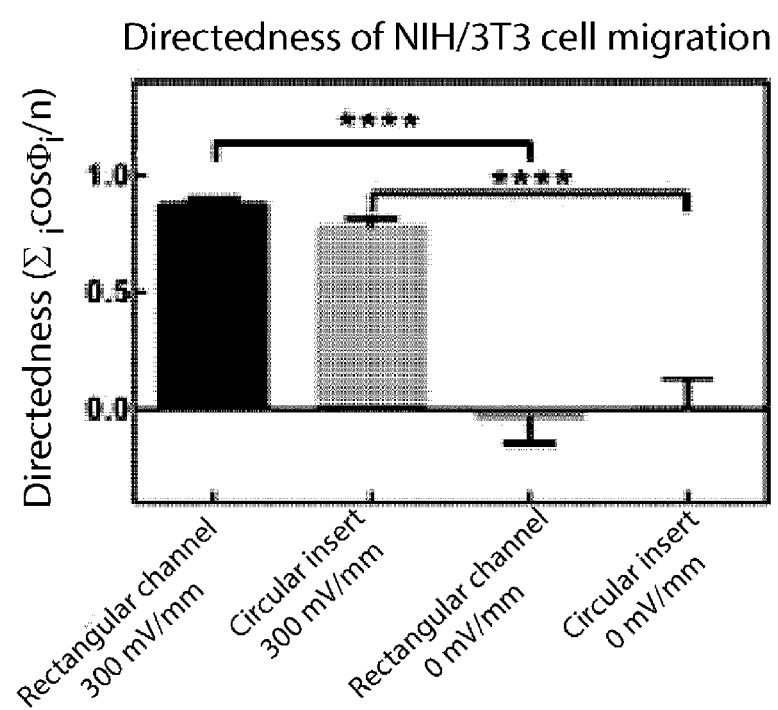

[Fig. 9(c)]
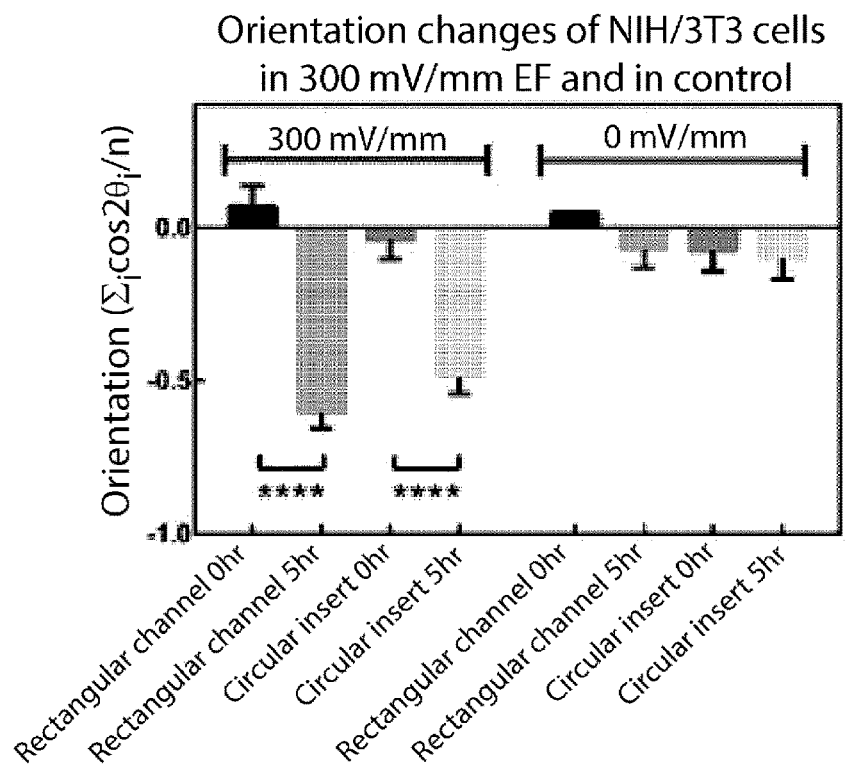
[Fig. 10]
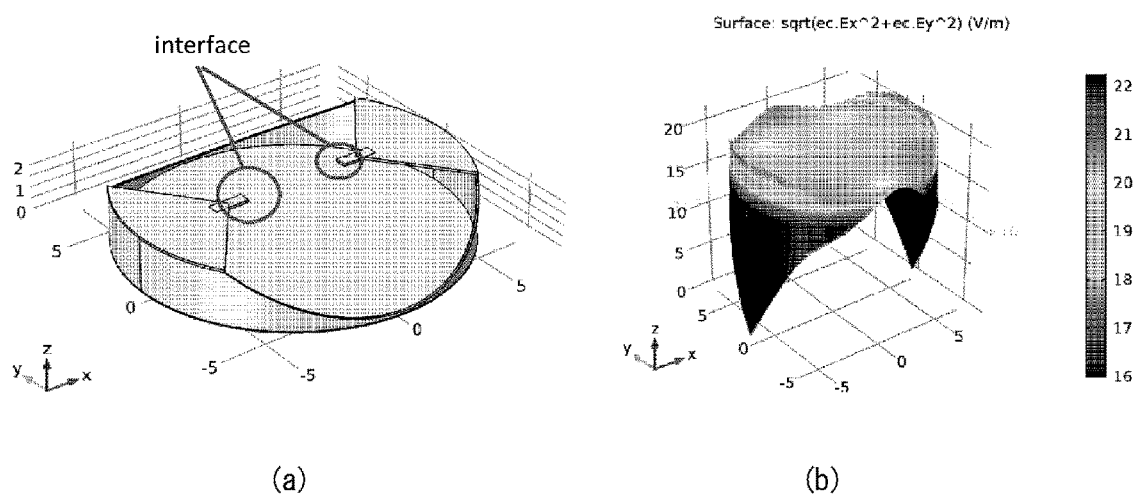
(a) (b)

[Fig. 11]
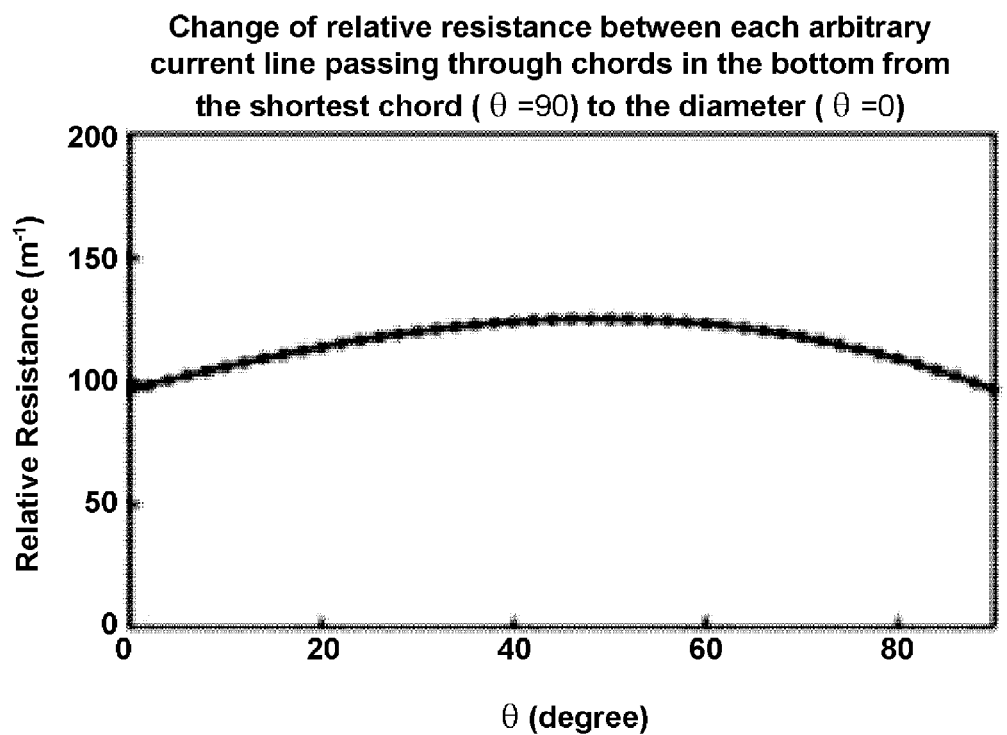

3D POLYMERIC INSERT TO APPLY UNIFORM ELECTRIC FIELD IN CIRCULAR CULTUREWARE

The present invention relates to circular culture plates for research and development in biological and similar fields. This application hereby incorporates by reference U.S. Provisional Application No. 62/220,841, filed Sep. 18, 2015, in its entirety.

TECHNICAL FIELD

Background Art

A weak direct-current electric field (dcEF) exists at the tissue level due to the transepithelial potential difference established by the tissue polarity (NPL No. 1). Cells demonstrate directional migration (electrotaxis) or orientation-change (electro-alignment) in response to a physiological dcEF in both in vitro and in vivo settings. The electrotaxis and dcEF stimulation have played pivotal roles in physiological processes such as embryonic development, neurogenesis, morphogenesis, and wound healing (NPL Nos. 1-5).

Numerous cellular signaling pathways have been regulated under electric field (EF) stimulation. Various membrane receptors (NPL Nos. 6-10) or ion channels (NPL Nos. 11-15) have been suggested to act as EF sensors and initiate many intracellular signaling cascades in different cell types (NPL Nos. 8, 13, and 16-21). Further investigations are required to clarify the functional roles of EF sensory proteins and signaling networks in regulating the electrotaxis phenomena.

Gaining a better understanding of signaling pathways demands a reliable and convenient electrical stimulation platform for microscopy imaging and cell product recovery with subsequent biochemical analysis. Even though an electrical cue can direct cell migration comparable to that of chemical cues (NPL No. 22) and synergistically promote directional migration with other physical factors such as shear stresses (NPL No. 23), electrotaxis is less well studied than chemotaxis, possibly due to the lack of experimental tools for convenient EF stimulation comparable to a boyden chamber (transwell chamber) that is routinely used for chemotaxis (NPL No. 24).

Conventional in vitro electrical stimulations were commonly performed either by direct stimulation using electrodes, or stimulation in a microfluidic chamber with salt bridges. The EF created through direct electrode stimulation is not uniform and cells are often exposed to toxic electrolysis products. Thus conventional electrotaxis studies usually employ a confined microfluidic chip in which cells are cultured in the bottom of the culture chamber (NPL Nos. 25-30). The small cross-section of the chamber limits the applicable electrical current and reduces the Joule heating that could be harmful to the cells.

Despite the success of using microfluidic chips for electrical stimulation in recent studies, these microfluidic chips often require special fabrication procedures on cell culture dishes days prior to the actual experiment, thereby limiting the adaptivity with common laboratory settings. Further, a simple rectangular shaped cell culture microchamber is usually placed on a circular shaped tissue-culture polystyrene (TCPS) petri dish to generate the uniform EF. As a result, a large portion of the cell culture area on the dish is unused, leading to a low cell yield and poor cell product recovery. Even though larger cell yields have been recently achieved by scaling up the rectangular shaped microchamber with increased cell culture area (NPL Nos. 29 and 30), a large fraction of the circular shaped TCPS dish is still unutilized. In a circular-shaped area, a uniform EF cannot be intuitively created by two electric potentials due to different electrical resistances originated from the length difference between the diameter of the circle and the length of any parallel chord of the bottom circular chamber where cells are cultured. For example, Marotta et al. electrically stimulated muscle cells to pace contraction by using a 6-well plate (NPL No. 31). A computer simulation indicates that the cells used in Marrotta et al. were subjected to non-uniform EF as well as electrolysis products. Furthermore, a computer simulation indicates that tissue pacing studies with a commercial electrical stimulation system suffered similar drawbacks (C-dishes, IonOptix, MA, USA) (NPL Nos. 32-35). Lin et al. used a modified transwell assay to study cell electrotaxis by applying EF through the transwell insert coupled with platinum electrodes (NPL No. 36). Alternatively, Garcia-Sanchez et al. used patterned electrodes to stimulate cells in multi-well plates (NPL No. 37). Their systems require sophisticated microfabrication procedures, and small EF-null gaps between electrodes also decrease the EF homogeneity. Recently, Ahirwar et al. used electromagnetic induction method with a boyden chamber to demonstrate non-contact directing electrotaxis, but non-uniform EF persisted (NPL No. 38).

Computer aided design and computer aided manufacturing (CAD/CAM) use computer software to precisely design model structure and program manufacturing processes. Mathematically depicted 3D structures for workpieces can be easily created by CAD/CAM software, and are conveniently adopted for numerical simulations. Thus, time, material, and manpower are greatly reduced for prototyping effort. In recent years, additive manufacturing (3D printing) (NPL No. 39) takes the advantage of CAD/CAM to rapidly prototype workpieces through layer-by-layer stacking of raw materials, and this technology has been used to fabricate microfluidic chips (NPL Nos. 40-43).

CITATION LIST

Non Patent Literature

NPL 1: McCaig, C. D., Song, B. & Rajnicek, A. M. Electrical dimensions in cell science. J Cell Sci 122, 4267-4276 (2009).

NPL 2: McCaig, C. D. Electric fields, contact guidance and the direction of nerve growth. J Embryol Exp Morphol 94, 245-255 (1986).

NPL 3: Messerli, M. A. & Graham, D. M. Extracellular Electrical Fields Direct Wound Healing and Regeneration. Biol Bull 221, 79-92 (2011).

NPL 4: Levin, M. Morphogenetic fields in embryogenesis, regeneration, and cancer: Non-local control of complex patterning. Biosystems 109, 243-261 (2012).

NPL 5: Golberg, A. et al. Skin Rejuvenation with Non-Invasive Pulsed Electric Fields. Scientific Reports 5, 10187 (2015).

NPL 6: Giugni, T. D., Braslau, D. L. & Haigler, H. T. Electric field-induced redistribution and postfield relaxation of epidermal growth factor receptors on A431 cells. J Cell Biol 104, 1291-1297 (1987).

NPL 7: Rochlin, M. W. & Peng, H. B. Localization of intracellular proteins at acetylcholine receptor clusters induced by electric fields in *Xenopus* muscle cells. J Cell Sci 94, 73-83 (1989).

NPL 8: McBain, V. A., Forrester, J. V. & McCaig, C. D. HGF, MAPK, and a Small Physiological Electric Field Interact during Corneal Epithelial Cell Migration. Investigative Opthalmology & Visual Science 44, 540 (2003).

NPL 9: Zhao, M., Bai, H., Wang, E., Forrester, J. V. & McCaig, C. D. Electrical stimulation directly induces pre-angiogenic responses in vascular endothelial cells by signaling through VEGF receptors. J Cell Sci 117, 397-405 (2004).

NPL 10: Zhang, H. L. & Peng, H. B. Mechanism of Acetylcholine Receptor Cluster Formation Induced by DC Electric Field. PLoS ONE 6, e26805 (2011).

NPL 11: Djamgoz, M. B. A., Mycielska, M., Madeja, Z., Fraser, S. P. & Korohoda, W. Directional movement of rat prostate cancer cells in direct-current electric field involvement of voltage-gated Na+ channel activity. J Cell Sci 114, 2697-2705 (2001).

NPL 12: Li, L. et al. Direct-Current Electrical Field Guides Neuronal Stem/Progenitor Cell Migration. STEM CELLS 26, 2193-2200 (2008).

NPL 13: Ozkucur, N., Monsees, T. K., Perike, S., Do, H. Q. & Funk, R. H. W. Local Calcium Elevation and Cell Elongation Initiate Guided Motility in Electrically Stimulated Osteoblast-Like Cells. PLoS ONE 4, e6131 (2009).

NPL 14: Ozkucur, N., Perike, S., Sharma, P. & Funk, R. H. Persistent directional cell migration requires ion transport proteins as direction sensors and membrane potential differences in order to maintain directedness. BMC Cell Biology 12, 4 (2011).

NPL 15: Perike, S. et al. Phospho-NHE3 forms membrane patches and interacts with beta-actin to sense and maintain constant direction during cell migration. Experimental Cell Research 324, 13-29 (2014).

NPL 16: McCaig, C. D. & Dover, P. J. Raised Cyclic-AMP and a Small Applied Electric Field Influence Differentiation, Shape, and Orientation of Single Myoblasts. Developmental Biology 158, 172-182 (1993).

NPL 17: Trollinger, D. R., Rivkah Isseroff, R. & Nuccitelli, R. Calcium channel blockers inhibit galvanotaxis in human keratinocytes. J. Cell. Physiol. 193, 1-9 (2002).

NPL 18: Zhao, M. et al. Electrical signals control wound healing through phosphatidylinositol-3-OH kinase-gamma and PTEN. Nature 442, 457-460 (2006).

NPL 19: Wartenberg, M. et al. Direct current electrical fields induce apoptosis in oral mucosa cancer cells by NADPH oxidase-derived reactive oxygen species. Bioelectromagnetics 29, 47-54 (2008).

NPL 20: Li, F. et al. Superoxide plays critical roles in electrotaxis of fibrosarcoma cells via activation of ERK and reorganization of the cytoskeleton. Free Radical Biology and Medicine 52, 1888-1896 (2012).

NPL 21: Guo, X. et al. The Galvanotactic Migration of Keratinocytes is Enhanced by Hypoxic Preconditioning. Scientific Reports 5, 10289 (2015).

NPL 22: Kao, Y.-C. et al. Modulating chemotaxis of lung cancer cells by using electric fields in a microfluidic device. Biomicrofluidics 8, 024107 (2014).

NPL 23: Song, S., Han, H., Ko, U. H., Kim, J. & Shin, J. H. Collaborative effects of electric field and fluid shear stress on fibroblast migration. Lab Chip 13, 1602-1611 (2013).

NPL 24: Boyden, S. The Chemotactic Effect of Mixtures of Antibody and Antigen on Polymorphonuclear Leucocytes. J Exp Med 115, 453-466 (1962).

NPL 25: Erickson, C. A. & Nuccitelli, R. Embryonic fibroblast motility and orientation can be influenced by physiological electric fields. J Cell Biol 98, 296-307 (1984).

NPL 26: Zhao, M., Agius-Fernandez, A., Forrester, J. V. & McCaig, C. D. Orientation and directed migration of cultured corneal epithelial cells in small electric fields are serum dependent. J Cell Sci 109, 1405-1414 (1996).

NPL 27: Song, B. et al. Application of direct current electric fields to cells and tissues in vitro and modulation of wound electric field in vivo. Nat. Protocols 2, 1479-1489 (2007).

NPL 28: Huang, C.-W., Cheng, J.-Y., Yen, M.-H. & Young, T.-H. Electrotaxis of lung cancer cells in a multiple-electric-field chip. Biosensors and Bioelectronics 24, 3510-3516 (2009).

NPL 29: Huang, C.-W. et al. Gene Expression of Human Lung Cancer Cell Line CL1-5 in Response to a Direct Current Electric Field. PLoS ONE 6, e25928 (2011).

NPL 30: Tsai, H.-F. et al. Evaluation of EGFR and RTK Signaling in the Electrotaxis of Lung Adenocarcinoma Cells under Direct-Current Electric Field Stimulation. PLoS ONE 8, e73418 (2013).

NPL 31: Marotta, M., Bragos, R. & Gomez-Foix, A. M. Design and performance of an electrical stimulator for long-term contraction of cultured muscle cells. BioTechniques 36, 68-73 (2004).

NPL 32: Genovese, J. A. et al. Electrostimulation induces cardiomyocyte predifferentiation of fibroblasts. Biochemical and Biophysical Research Communications 370, 450-455 (2008).

NPL 33: Okutsu, S., Hatakeyama, H., Kanazaki, M., Tsubokawa, H. & Nagatomi, R. Electric Pulse Stimulation Induces NMDA Glutamate Receptor mRNA in NIH3t3 Mouse Fibroblasts. The Tohoku Journal of Experimental Medicine 215, 181-187 (2008).

NPL 34: Yamasaki, K.-i. et al. Control of myotube contraction using electrical pulse stimulation for bio-actuator. Journal of Artificial Organs 12, 131-137 (2009).

NPL 35: Burch, N. et al. Electric Pulse Stimulation of Cultured Murine Muscle Cells Reproduces Gene Expression Changes of Trained Mouse Muscle. PLoS ONE 5, e10970 (2010).

NPL 36: Lin, F. et al. Lymphocyte Electrotaxis In Vitro and In Vivo. J Immunol 181, 2465-2471 (2008).

NPL 37: Garcia-Sanchez, T. et al. Design and Implementation of a Microelectrode Assembly for Use on Noncontact In Situ Electroporation of Adherent Cells. J Membrane Biol 245, 617-624 (2012).

NPL 38: Ahirwar, D. K. et al. Non-contact method for directing electrotaxis. Scientific Reports 5, 11005 (2015).

NPL 39: Sachs, E., Cima, M., Williams, P., Brancazio, D. & Cornie, J. Three Dimensional Printing: Rapid Tooling and Prototypes Directly from a CAD Model. J. Eng. Ind 114, 481-488 (1992).

NPL 40: Waldbaur, A., Rapp, H., Lange, K. & Rapp, B. E. Let there be chip-towards rapid prototyping of microfluidic devices: one-step manufacturing processes. Anal. Methods 3, 2681-2716 (2011).

NPL 41: Waldbaur, A., Carneiro, B., Hettich, P., Wilhelm, E. & Rapp, B. E. Computer-aided microfluidics (CAMF): from digital 3d-CAD models to physical structures within a day. Microfluid Nanofluid 15, 625-635 (2013).

NPL 42: Shallan, A. I., Smejkal, P., Corban, M., Guijt, R. M. & Breadmore, M. C. Cost-Effective Three-Dimensional Printing of Visibly Transparent Microchips within Minutes. Anal. Chem. 86, 3124-3130 (2014).

NPL 43: Ho, C. M. B., Ng, S. H., Li, K. H. H. & Yoon, Y.-J. 3d printed microfluidics for biological applications. Lab Chip 15, 3627-3637 (2015).

NPL 44: Tsai, H.-F., Peng, S.-W., Wu, C.-Y., Chang, H.-F. & Cheng, J.-Y. Electrotaxis of oral squamous cell carcinoma cells in a multiple-electric-field chip with uniform flow field. Biomicrofluidics 6, 34116 (2012).

NPL 45: Hobbie, R. K. & Roth, B. J. Intermediate Physics for Medicine and Biology (Springer, 2015).

NPL 46: Larson, R. & Edwards, B. H. Calculus Multivariable (Cengage Learning, 2009).

NPL 47: Cheng, J.-Y., Wei, C.-W., Hsu, K.-H. & Young, T.-H. Direct-write laser micromachining and universal surface modification of PMMA for device development. Sensors and Actuators B: Chemical 99, 186-196 (2004).

NPL 48: Cheng, J.-Y., Yen, M.-H., Kuo, C.-T. & Young, T.-H. A transparent cell-culture microchamber with a variably controlled concentration gradient generator and flow field rectifier. Biomicrofluidics 2, 24105 (2008).

NPL 49: Brown, M. J. & Loew, L. M. Electric field-directed fibroblast locomotion involves cell surface molecular reorganization and is calcium independent. J Cell Biol 127, 117-128 (1994).

NPL 50: Finkelstein, E. et al. Roles of microtubules, cell polarity and adhesion in electric-field-mediated motility of 3t3 fibroblasts. J Cell Sci 117, 1533-1545 (2004).

NPL 51: Huang, Y.-J., Samorajski, J., Kreimer, R. & Searson, P. C. The Influence of Electric Field and Confinement on Cell Motility. PLoS ONE 8, e59447 (2013).

NPL 52: Tandon, N. et al. Electrical stimulation systems for cardiac tissue engineering. Nat. Protocols 4, 155-173 (2009).

NPL 53: Babona-Pilipos, R., Droujinine, I. A., Popovic, M. R. & Morshead, C. M. Adult subependymal neural precursors, but not differentiated cells, undergo rapid cathodal migration in the presence of direct current electric fields. PLoS ONE 6, e23808 (2011).

NPL 54: McDonough, P. M. & Glembotski, C. C. Induction of atrial natriuretic factor and myosin light chain-2 gene expression in cultured ventricular myocytes by electrical stimulation of contraction. J. Biol. Chem. 267, 11665-11668 (1992).

NPL 55: Radisic, M. et al. Functional assembly of engineered myocardium by electrical stimulation of cardiac myocytes cultured on scaffolds. Proc. Natl. Acad. Sci. U.S.A. 101, 18129-18134 (2004).

NPL 56: Serena, E. et al. Electrical stimulation of human embryonic stem cells: Cardiac differentiation and the generation of reactive oxygen species. Experimental Cell Research 315, 3611-3619 (2009).

NPL 57: Barash, Y. et al. Electric Field Stimulation Integrated into Perfusion Bioreactor for Cardiac Tissue Engineering. Tissue Engineering Part C: Methods 16, 1417-1426 (2010).

NPL 58: Hronik-Tupaj, M., Rice, W. L., Cronin-Golomb, M., Kaplan, D. L. & Georgakoudi, I. Osteoblastic differentiation and stress response of human mesenchymal stem cells exposed to alternating current electric fields. BioMedical Engineering OnLine 10, 9 (2011).

NPL 59: Marotta, M., Bragos, R. & Gomez-Foix, A. M. Design and performance of an electrical stimulator for long-term contraction of cultured muscle cells. BioTechniques 36, 68-73 (2004).

NPL 60: Hobbie, R. K. & Roth, B. J. Intermediate Physics for Medicine and Biology (Springer, 2015).

NPL 61: Larson, R. & Edwards, B. H. Calculus Multivariable (Cengage Learning, 2009).

SUMMARY OF INVENTION

Technical Problem

The conventional techniques described above have not yet provided convenient and efficient means for creating reliable uniform electric field in circular culture plate/cultureware.

An object of the present invention is to provide an efficient and very effective way to establish a uniform electric field in circular culture plate/cultureware.

Solution to Problem

To achieve these and other advantages and in accordance with the purpose of the present invention, as embodied and broadly described, in one aspect, the present invention provides an insert to be inserted into a circular-shaped petri dish for generating a substantially uniform electric field across the petri dish filled with a fluid establishing a salt bridge, comprising: a circular-shaped bottom plate configured to be fitted into the circular-shaped petri dish, the bottom plate defining a circular-shaped space of a substantially uniform thickness together with a circular-shaped bottom surface of the petri dish as a channel accepting said fluid when the insert is inserted into the petri dish; a side channel vertically erecting from a circular periphery of said bottom plate, the side channel communicating with said circular shaped space defined by the bottom plate so as to accept said fluid; and a pair of current rectifying chambers each having a generally planar shape connecting to and communicating with the side channel, the current rectifying chambers being diagonally disposed to face each other along a diameter of the circular shaped bottom plate and being line-symmetric with each other with respect to said diameter, each of the current rectifying chambers extending inwardly from a respective portion of a top end of the side channel and having a salt bridge port to accept the fluid and provide the fluid to said circular-shaped space defined by the bottom plate through said side channel so as to establish the salt bridge, wherein portions of the side channel other than the portions thereof respectively connecting to the current rectifying chambers each have a generally concave top profile having a lowest point at a center between the pair of current rectifying chambers and are each shaped such that when the salt bridge is established, the circular-shaped space defined by the bottom plate exhibits a uniform electric field in a direction of said diameter in a substantially entire area thereof.

Here, the circular shaped petri dish may be a tissue-culture polystyrene (TCPS) petri dish. Said generally concave top profile of the side channel may outline a curve defined by an intersection of a paraboloid with a cylindrical column. Further, said generally concave top profile of the side channel may have a stair-like shape outlining said curve.

In another aspect, the present invention provides a device for establishing a uniform electric field in a planar circular-shaped space filled with a fluid having a prescribed resistivity, comprising a unitary or multipart member that defines: the planar circular-shaped space of a substantially uniform thickness; a side channel vertically erecting from a circular periphery of said planar circular-shaped space; and a pair of planar chambers each connecting to and communicating with the side channel, the planar chambers being diagonally disposed to face each other along a diameter of the planar circular-shaped space and being line-symmetric with each other with respect to said diameter, each of the planar chambers extending inwardly from a respective portion of a top end of the side channel and having a port to accept the fluid and provide the fluid to said planar circular-shaped space through said side channel, each port being configured to be applied with a prescribed voltage when the planar circular-shaped space, the side channel and the planar chambers are filled with the fluid, wherein portions of the side channel other than the portions thereof respectively connecting to the planar chambers each have a generally concave top profile having a lowest point at a center between the pair of planar chambers and are each shaped such that when filled with the fluid and said prescribed voltages are applied, the planar circular-shaped space exhibits a uniform electric field in a direction of said prescribed diameter in a substantially entire area thereof.

Here, said unitary or multipart member may comprise an insert and a circular-shaped petri dish to which the insert is inserted, together defining said planar circular-shaped space, said side channel, and said pair of planar chambers.

Advantageous Effects of Invention

According to one or more aspects of the present invention, a uniform electric field can be established in circular culture plates/cultureware, which can be used in various research and development efforts in the biological and similar academic and industrial fields.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

It is to be understood that both the foregoing general description and the following detailed description are exemplary and explanatory, and are intended to provide further explanation of the invention as claimed.

BRIEF DESCRIPTION OF DRAWINGS

FIG. 1(a) is a schematic diagram of electrical stimulation setup by using the 6-layered PMMA insert for uniform EF stimulation on cells according to an embodiment of the present invention.

FIG. 1(b) shows a schematic of the layered insert (not to scale) of FIG. 1(a). PMMA top assembly containing current rectifying chambers (CRC) and 3D CAD structures are affixed to the cell culture dish through a piece of double sided tape to form the assembled microfluidic chip. Here, salt bridge is abbreviated as SB.

FIG. 1(c) shows a schematic of the simple rectangular channel chip (not to scale). The PMMA containing a world-to-chip interface was affixed to the cell culture dish through a piece of double sided tape containing two rectangular channels to form the assembled microfluidic chip.

FIG. 2(a) shows an overall three-dimensional structure of a fluid channel, i.e., a space in which a fluid is filled, defined by an insert of an embodiment of the present invention. This figures shows a 3D CAD principle according to an embodiment of the present invention. The structure of the top assembly is shown in dark grey, which is formed by intersecting the liquid column (LC) with two paraboloids (P1&P2, light grey).

FIG. 2(b) shows a three-dimensional structure of a fluid channel created by a plain polymeric insert that does not have the structure of the present invention. The liquid column is shown in the drawing. Salt bridges are abbreviated as SB. Current rectifying chambers are abbreviated as CRC.

FIG. 2(c) shows a three-dimensional structure of a fluid channel defined by a polymer insert according to an embodiment of the present invention, which is to be inserted in a 6-well plate. As shown in the figure, this insert is assumed to have a smooth sidewall profile, which is ideal. FIG. 2(d) shows a three-dimensional structure of a fluid channel defined by a polymer insert according to an embodiment of the present invention, in which rather than ideal smooth sidewall profile, a more practical layered structure is adopted in constructing the insert (hence a layered sidewall shape) that approximates an ideal structure depicted in FIG. 2(c).

FIG. 3 shows the workflow of the cell experiment by using the polymeric insert. As shown in (a), that the insert was affixed to the dish first. PBS, cell culture medium, and cell suspension were infused into the microfluidic chip sequentially. Alternatively, as show in (b), to further avoid bubble entrapment, the insert can be affixed to the dish in PBS. Thereafter, the buffer is replaced by cell culture medium and cell suspension is then inoculated.

FIG. 4 shows COMSOL simulation results. (a) shows the current density in a plain polymeric insert. (b) shows the current density in a smooth 3D CAD insert according to an embodiment of the present invention. (c) shows that the current density in a layered PMMA insert according to an embodiment of the present invention. (d) shows the EFS at the bottom of the chamber with the plain polymeric insert. (e) shows the EFS at the bottom of the chamber with the smooth 3D CAD insert. (f) shows the EFS at the bottom chamber with the layered PMMA insert.

FIG. 5 shows tolerance of EF uniformity to the thickness of the chamber in a CAD insert, examined by numerical simulations. With the increased thickness of the bottom chamber thickness from 0.2 mm to 0.3 mm, the resistance decreases and the mean EFS slightly increases (see dark circles). But the simulated mean EFSs in the chamber with this thickness range are very close to the intended value of 100 mV/mm. The coefficient of variation (CV) describing the non-uniformity in the EFS is the lowest in the intended 0.26 mm-thick chamber. Nevertheless, the CVs in all thickness examined are below 3%, verifying the robustness of the CAD insert for creating a uniform EF (see light squares).

FIG. 6 shows results of numerical simulations of scaled-up inserts for a 100 mm tissue culture polystyrene dishes according to embodiments of the present invention. (a) shows CAD model for the fluid channel created by the insert with paraboloid smooth surfaces. (b) shows the uniform EF created by the structure of (a). (c) shows a corresponding 6-layered PMMA insert, and (d) shows the uniform EF created in the structure of (c). In the smooth 3D CAD model of (b), the mean EFS and the CV of the EFS are 97.44±1.47 mV/mm and 1.51%. The mean EFS and the CV of the EFS in the layered insert (d) are 94.73±1.59 mV/mm and 1.67%. The layered inset of (c) is relatively less ideal than the smooth 3D CAD model of (a) due to its rough surfaces but it does not affect the uniformity of the EF stimulation, and is still acceptable.

FIG. 7 shows the measured EFS in the insert as a mesh plot in which the standard deviations are shown in black error bars. Note that the error in each position is low.

FIG. 8 shows the phase contrast microscopy images of NIH/3T3 cells after 5 hours of cell migration and alignment experiment with the circular polymeric insert: (a) without EF stimulation; (b) with 300 mV/mm EF stimulation.

FIG. 9(a) shows the schematic representation of the angle to calculate directedness and orientation used in quantification of the cell migration and alignment measurements for the NIH/3T3 cells the images of which are shown in FIG. 8.

FIG. 9 (b) shows the resulting directedness of cell migration comparing cases of a rectangular channel and a circular insert of the embodiment of the present invention with and without EF stimulation in the cell migration and alignment measurements.

FIG. 9(c) shows the resulting orientation of the cell migration comparing cases of the rectangular channel and the circular insert of the embodiment of the present invention with and without EF stimulation in the cell migration and alignment measurements. Four asterisks indicate $p<0.0001$ from Dunn's post-hoc test.

FIG. 10 shows numerical simulation results of an insert for 15 mm well in 24-well plate according to another embodiment of the present invention. (a) shows a structure of the fluid channel of the embodiment for which EF evaluation was performed by simulation. (b) shows a simulation result of EF distribution.

FIG. 11 shows the change in relative resistance between each arbitrary current line passing through each chord in the bottom chamber from the shortest chord to the diameter, by varying 0 from 0 degree to 90 degrees.

DESCRIPTION OF EMBODIMENTS

As discussed above, applying uniform electric field (EF) in vitro in the physiological range has been achieved in rectangular shaped microchannels. However, in a circular-shaped device, it has been difficult to create uniform EF from two electric potentials due to different electrical resistances originated from the length difference between the diameter of the circle and the length of any parallel chord of the bottom circular chamber where cells are cultured. To address this challenge, the present disclosure provides a three-dimensional (3D) computer-aided designed (CAD) polymeric insert to create uniform EF in circular shaped multi-well culture plates/cultureware. In some embodiments, a uniform EF with a coefficient of variation (CV) of 1.2% in the 6-well plate can be generated with an effective stimulation area percentage of 69.5%. In particular, NIH/3T3 mouse embryonic fibroblast cells are used to validate the performance of the 3D designed Poly(methyl methacrylate) (PMMA) inserts in a circular-shaped 6-well plate. The CAD based inserts can be easily scaled up (i.e., 100 mm dishes) to further increase effective stimulation area percentages, and also be implemented in commercially available cultureware for a wide variety of EF-related research such as EF-cell interaction and tissue regeneration studies. In some embodiments, using Ohm's law, an optimized CAD structure is created to equalize the electrical resistance in the circular shaped bottom chamber to generate a uniform EF. As a result, a large area of contemporary cell culture dish can be stimulated with the uniform EF, and a higher cell yield can be obtained.

<Material and Methodology>
<Microfluidic Chip Composition and Assembly>

The schematic diagram of an electrical stimulation setup using an assembled microfluidic chip according to an embodiment of the present invention is shown in FIG. 1(a). The entire microfluidic assembly in this embodiment consists of two main compartments. The bottom structure is a standard tissue culture polystyrene (TCPS) dish, which was mounted on an indium tin oxide (ITO) transparent heater on the microscope stage for temperature control required for cell culture operation (NPL No. 44). An insert part was affixed to the TCPS dish by a double sided tape adhered to the inner side of the dish (see FIG. 1(b)) (NPL No. 30). The polymeric insert was fabricated in layered Poly(methyl methacrylate) (PMMA) based on 3D computer-aided design to provide current rectifying chambers (CRC) and accommodate inlet, outlet, and salt bridges (SB) tubing interfaces. To conform the effectiveness of the insert of the present embodiment for electrotaxis, a simple microdevice with rectangular channels was fabricated and used as a reference system for comparison purpose (FIG. 1(c)). Two identical rectangular channels (30 mm×3 mm×0.07 mm, L×W×H) were designed in a single chip. Similar channel dimensions have been used to study the electrotaxis of many cell lines (NPL No. 28).

<Design Principle>

As discussed above, a uniform EF cannot be simply created in a circular area due to different electrical resistances originated from the length difference between the diameter of the circle and the length of any parallel chord. Creating a uniform EF in a circular shaped chamber with the largest possible surface area for cells is therefore challenging. As illustrated in FIG. 2(a), cells occupy the bottom region of the bottom chamber (xy plane with diameter $\overline{BC}$, with its centroid on the y-axis). The insert on top of the red region contains a thin liquid column (LC), residing on top of the bottom chamber. The assembled microdevice contains the bottom chamber, liquid column, and the current rectifying chambers (CRC, also termed as world-to-chip interface). See FIGS. 2(b) to 2(d), for example. An electrical current flowing from one salt bridge (i.e., A) to the other (i.e., D) cannot create a uniform EF in the bottom chamber without any structural modifications on sidewall channel, such as shown in FIG. 2(b). To create a uniform EF, a structure must be such that the electrical resistance from one salt bridge to the other through any cross-section in the system must be the same so that all the electrical currents must pass through the bottom chamber uniformly.

To address this challenge, the present disclosure uses CAD to design a structure in which the electrical resistances through any arbitrary current paths that pass through the bottom circular chamber are substantially the same among each other. The resulting ideal structure is shown in FIG. 2(a), which is obtained from intersecting the liquid column (i.e., cylindrical sidewall LC) by two identical circular paraboloids ($P_1$ and $P_2$) whose apexes are located at the intersects of the midline of the $\overline{AD}$ and the liquid column LC (FIG. 2(a)). Thus, in this cylindrical structure, the top profile of the sidewall is curved by the intersects. The remaining structure is an ideal microfluidic channel (i.e., a channel in which a fluid can be filled). In this figure, the apex O of the paraboloid P1 coincides with the origin of the coordinate system. The paraboloid intersects with the liquid column at the curve $\overline{AOD}$ (white dashed curve, FIG. 2(a)) where the projection of points A and D on xy plane are B and C. The electrical resistance can be calculated by considering both the length and the cross-sectional area according to Ohm's law (NPL No. 45). To facilitate a uniform EF in the bottom chamber, the electrical resistance passing through curve $\overline{AOD}$ must be equal to that through $$\overline{AB}+\overline{BC}+\overline{CD}$$

(solid line connecting A, B, C and D). In other words, the electrical current passing along the parabolic curve $$\overline{AOD}$$

should hold the same strength to the electrical current passing through $$\overline{AB}+\overline{BC}+\overline{CD}.$$

The arc length of curve $$\overline{AOD}$$

can be determined by using multivariate calculus (NPL No. 46). See detailed derivation and the design principle explained in a section below, entitled "Detailed Design Procedure." In short, the constant of the paraboloids describing the level of curvature in xz and yz planes and the height of the liquid column can be calculated and used for model design in a commercial CAD software package (Rhinoceros, USA). The resulting structure is illustrated in FIG. 2(c).

Note that in FIG. 2(c), an ideal structure depicted in FIG. 2(a) is modified due to the need to have Salt bridge ports SB, and current rectifying chambers CRC which communicate with the remaining sidewall-shaped channel, and eventually communicate with the bottom part once the insert is inserted in a circular cultureware, for example. As compared to FIG. 2(b), the top profile of the side channel in FIG. 2(c) has a concave shape defined by the intersects.

<Numerical EF Simulation>

The CAD model for a plain polymeric insert, created by the aforementioned principle, was imported into COMSOL Multiphysics software (COMSOL Inc., USA). The model used the culture medium (Dulbecco's minimum essential medium, DMEM) as the ionic fluid that is filing in the created fluidic channel (having a shaped shown in the figures mentioned above), and the electric potential between the salt bridges SB was numerically simulated by solving steady-state Maxwell's equations using the alternating current/direct current (AC/DC) module in COMSOL for the structures of the fluidic channels shown in FIGS. 2(b) and 2(c) (FIG. 2(b) being a comparative example). The conductivity of DMEM was measured to be 1.515 S/m (F74 with 3553-10D conductivity probe, Horiba, Japan), and this value was input in the COMSOL. A current density of 376.1 A/m2 aimed to create 100 mV/mm EF was set as the boundary condition at one salt bridge connection, and a ground potential was set at the other salt bridge. The electric field strength (EFS) at the bottom of the cell culture chamber were analyzed to assess the EF uniformity at a height of 10 μm. The EFS data points at positions where the liquid column resides were excluded. The numerical simulation results were exported and analyzed in Prism 6 software (Graphpad, USA).

Due to the limitation of in-house fabrication tools, the assembled microfluidic chip based on the 3D CAD model with smooth paraboloid surface was not fabricated in this work. Instead, an approximated 6-layered model shown in FIG. 2(d) compatible with PMMA thermoplastic manufacturing procedure was applied. This 6-layered PMMA insert possessed the same thickness (6 mm) as the original plain 3D CAD model and the same paraboloid parameters were employed in the fabrication. Based on this proof of concept study, the 3D CAD insert can be easily manufactured by computer numerical control (CNC) manufacturing technologies in the future. To examine the robustness of creating the uniform EF by using layered inserts, the tolerance of the EFS and uniformity to different cell chamber thickness ranging 0.2-0.3 mm was also simulated for the structure shown in FIG. 2(d).

<Device Fabrication and EF Measurements>

The 6-layered approximation model for both 6-well plates and 35 mm dishes was used for the fabrication of inserts. Patterns were designed in AutoCAD software (Autodesk, USA) and a 1 mm thick PMMA substrate (Comoglas, Kuraray, Japan) was cut based on the 3D design by using a CO2 laser cutter (VLS2.30, Universal Laser Systems, USA). The layers were aligned and joined by thermal bonding and polymeric tapes (FIG. 1(b)). The same fabrication procedure as previously reported (NPL Nos. 47 and 48) was used. See these articles for details. Adapters for fitting connection were super-glued onto the inserts (406 Prism Instant Adhesive, Loctite, USA). The double sided tape for the insert was then affixed to the insert bottom (0.26 mm-thick, F9473PC, 3M, USA). The fabrication process of the simple rectangular channel chip shown in FIG. 1(c) followed the same procedure as those for the circular insert.

To measure the EF in the bottom chamber in the insert, an array of holes in 0.3 mm diameter were drilled on the 1 mm-thick PMMA substrate (NPL Nos. 25 and 28). The spacing between each hole was 3 mm. The holes were temporarily sealed with a Kapton tape. The insert was filled with Dulbecco's minimum essential medium (DMEM, 12800017, Gibco, USA). A 46 V electric potential was applied through Ag/AgCl electrodes (25 mm×100 mm) by a DC power supply (E3641A, Keysight technologies, USA). Preparation of Ag/AgCl electrodes described in NPL No. 30 was used. To measure the voltage differences, two Ag/AgCl wire based electrodes (0.3 mm diameter) were inserted into two adjacent holes after piercing the tape cover (NPL Nos. 30 and 44). The voltage differences between any two electrodes in the chamber were measured by a digital multimeter (2100, Keithley Instruments, USA) for 20 samples at every position by using the Excel add-in function provided by the manufacturer (KI-LINK, Keithley Instruments, USA). The EFSs can then be calculated by dividing the voltage differences by the distance between respective electrodes. The results of mean EFSs and standard deviations are calculated and exported using a custom MATLAB script (Mathworks, USA). See Table 1 below.

<Cell Culture and Maintenance>

A Swiss murine embryonic fibroblast cell line with 3-day transfer protocol, NIH/3T3 (American Type Culture Collection, ATCC, USA) was used to demonstrate the electrical stimulation functionality with the polymeric circular insert and the rectangular microchannel described above. The cells were cultured on TCPS dishes in DMEM supplemented with 10% fetal bovine serum (FBS, Sigma-Aldrich, USA) at 37 degrees Celsius in a 95% relative humidity atmosphere supplemented with 5% $CO_2$. The cells were sub-cultured twice a week by the recommended split ratio with trypsin-EDTA (Life Technologies, USA). For long term storage, the cells supplemented with 10% dimethylsulfoxide were cryopreserved in liquid nitrogen.

<EF Stimulation and Microscopy Analysis>

Each six-layered PMMA insert was disinfected and then affixed to individual wells in a 6-well TCPS plate or to a 100 mm TCPS dish (see FIG. 1(b)). Similar procedure was applied to the simple rectangular channel chip. To avoid entrapment of bubbles, which could disrupt EF uniformity and cause cell death, assembled microfluidic chips were primed by $CO_2$ gas, and filled with phosphate buffered saline (PBS, Life Technologies, USA) as shown in FIG. 3(a).

Alternatively, the inserts can be affixed to the well bottom with the presence of PBS as shown in FIG. 3(b) to further reduce bubble entrapment because the double sided tape has a limited adhesiveness in protein-free buffer solution.

To start the cell experiment, PBS pre-filled chamber was first replaced by serum-containing cell culture medium, and a suspension of $5 \times 10^5$ cells was subsequently loaded into the chamber through the salt bridge ports by gravity feeding. After overnight culture for cell adhesion and growth, fittings to supply culture medium and for salt bridges (containing 1.2% agarose (LE agarose, Lonza, USA) in PBS) were connected to the top of the inserts. A syringe pump (YSP-202, YMC, Japan) was used to exchange cell culture medium during the time lapse experiment at a flow rate of 100 µL/h for the circular insert and 20 µL/h for the rectangular channels to obtain similar shear stress acting on the cells. A DC voltage and the current was applied and measured by a high voltage source meter unit (2410, Keithley Instruments, USA) through Ag/AgCl electrodes in PBS. The required current for a 300 mV/mm EF in a chamber of 30 mm in diameter and 0.26 mm in thickness was 3.545 mA.

The time lapse electrotaxis experiments were carried out on an automated microscope (Ti-E, Nikon, Japan). The phase contrast cell images were taken at different positions across the devices at an interval of 5 minutes. The morphology and centroid of cells were tracked manually for the duration of 5 hour time lapse using ImageJ analysis software package. All data are represented as the mean 95% confidence interval, which is 1.96 of standard error of mean, from triplicate experiments. Kruskal-Wallis one-way analysis of variance on ranks test with Dunn's multiple comparison post-hoc test were performed when non-Gaussian distribution of sample data was obtained from Bartlett's test. The confidence level to reject a null hypothesis between two data sets was set at 95%. A p-value (the probability for a true null hypothesis) less than 0.05 represents a statistical significance at 95% confidence.

<Results and Considerations>
<3D CAD Optimization for Uniform EF Creation>

The current density at the bottom of the chamber was simulated for the plain polymeric insert illustrated in FIG. 2(b), the smooth polymeric insert with the 3D structure designed to intersect a liquid column by paraboloids according to an embodiment of the present invention, illustrated in FIG. 2(c), and the layered approximation for the PMMA insert according to an embodiment of the present invention, illustrated in FIG. 2(d). With the liquid column height of 0.5 mm, uniform EF can be obtained for a 0.26 mm thick chamber using a 6 mm thick insert. A 6 mm thick insert can also be designed for a 0.13 mm thick chamber by decreasing the liquid column thickness to 0.25 mm.

The simulated EF results for the plain polymeric insert, the smooth 3D CAD insert, and layered 3D CAD inserts are shown in FIG. 4. FIG. 4 shows that without the 3D designed structure according to embodiments of the present invention, a large portion of the electrical current passes through the liquid column (side wall channel) instead of passing through the bottom chamber where the cells are located (FIG. 4(a)) and creates a non-uniform EF (FIG. 4(d)). With the 3D designed structure, the current lines are uniformly distributed in the bottom chamber, indicating that a uniform and directional EF was created (FIG. 4(b)). The highly directional EF created by using the insert also suggests that the inserts are suitable not only for cell stimulation but also for electrotaxis studies. FIG. 4(e) shows the excellent uniformity of the EFS in the smooth 3D CAD insert. Further, a desired uniform decrease in the electric potential in the bottom chamber was confirmed. FIGS. 4(c) and 4(f) indicate that a uniform and directional EF being created by the approximated layered PMMA insert, the fluid channel structure of which is illustrated in FIG. 2(d).

TABLE 1

Simulated mean EFS and CV from polymeric inserts with the bottom chamber at the height of 0.26 mm and 0.13 mm

|  |  | 0.26 mm thick | | 0.13 mm thick | |
| --- | --- | --- | --- | --- | --- |
|  |  | EFS (mV/mm) | CV | EFS (mV/mm) | CV |
| 6-well | Plain | 75.03 ± 5.94 | 7.91% | 74.0 ± 10.06 | 6.80% |
|  | 3D CAD | 96.10 ± 1.18 | 1.22% | 96.47 ± 1.38 | 1.43% |
|  | Layered | 89.06 ± 1.63 | 1.30% | 88.92 ± 1.69 | 1.90% |
| 100 mm | 3D CAD | 97.44 ± 1.47 | 1.51% | 97.29 ± 2.61 | 2.68% |
|  | Layered | 94.73 ± 1.59 | 1.67% | 94.55 ± 2.72 | 2.88% |

The simulated results are summarized in Table1. In the plain polymeric insert without the 3D designed structure, the EF is non-uniform and the mean EFS and the coefficient of variation (CV, defined as the ratio of the standard deviation to the mean) are 75.03 mV/mm and 7.91%. In the 6-well plate (or a 35 mm dish) with the smooth CAD designed insert, an EF with mean EFS of 96.1 mV/mm is established with a 1.22% CV. As shown in Table 1, due to the rough surface in the layered approximation PMMA insert, the EF is less uniform than that in the smooth 3D CAD insert, which has smooth paraboloid surfaces. However, the layered PMMA insert can still create a very good uniform and directional EF, with mean EFS of 89.1 mV/mm and a CV of 1.30%, which is acceptable.

The double sided tape used in this study is a pressure sensitive adhesive prone to deformation under pressure or stretching. Effect of slight deformation in the chamber thickness to the EF uniformity was examined by numerical simulations. FIG. 5 shows the tolerance of mean EFS and CV in chamber thickness ranging from 0.2 mm to 0.3 mm. Although the chamber with a height of 0.26 mm has the smallest CV, all the simulation data of CV are smaller than 3%, demonstrating the versatility of the 3D CAD inserts presented herein.

The 3D CAD approach can be easily adapted to further scale up the insert for larger petri dishes such as 100 mm TCPS dishes. Uniform EFs are established in both a theoretical smooth 3D insert and an approximated layered PMMA insert with a height of 10 mm for a 100 mm dish as shown in Table 1 above and FIG. 6. This demonstrates the flexibility of the 3D CAD procedure and principle accordingly to the present invention for creating a uniform EF in a circular shaped device.

<Validation of EF Uniformity in the Chamber>

FIG. 7 shows the experimentally measured EFS in the bottom chamber by the Ag/AgCl wire electrodes. The EFSs were measured between adjacent holes parallel to the electric current vector. The result shows that EFS of all measurement is 141.4±1.3 mV/mm with a CV of 0.92%, suggesting that a highly uniform EF is created in the bottom chamber. The 46 V electric potential created an expected 150 mV/mm EFS in the bottom chamber. The measured mean EFS is about 94.3% of the expected value, which coincides with the measurement errors reported in previous studies (NPL Nos. 29 and 30). The CV of the measured EFSs is comparable to the 1.30% value expected from numerical simulation (see Table 1 above). This value is also comparable to the 2.3% CV of measured EFS from the largest rectangular electrical stimulation device reported previously (NPL No. 30). Finally, the EFSs along the perpendicular direction to the electric current vector is measured to be 4.68±1.90 mV/mm, only 3% of that in the parallel direction. Thus, actual measurement of electric field strength confirms efficacy of the present invention.

<High Performance Cell EF Stimulation>

While the conventional in-vitro electrical stimulation devices either sacrifice the culture area to stimulate cells uniformly, or stimulate large areas of cells with non-uniform EF, the polymeric circular inserts developed in this disclosure can provide uniform EF stimulation to large area percentage of cells. The effective stimulation area is defined as the area of the bottom chamber subtracting the area of where the liquid column resides. The effective stimulation area percentage is the ratio of the effective stimulation area over the total surface area of the TCPS dish.

Table 2 below lists the effective stimulation area percentages using the polymeric inserts of the present disclosure and those reported in other literatures. As shown in Table 2, most existing devices cannot achieve uniform EF stimulation in more than 50% of the total cell culture area. In contrast, polymeric inserts according to embodiment of the present invention can provide uniform EF stimulation in more than 69% of the total area in a 6-well plate (or a 35 mm dish), and up to 90% in a 100 mm petri dish. Thus, the cell yields are higher when using polymeric inserts of the present invention for electrical stimulation. The higher cell yields will greatly benefit biochemical and molecular biology analysis.

cells after 5 hours of experiment with the circular polymeric insert: (a) without EF stimulation; (b) with 300 mV/mm EF stimulation.

To quantify the cell migration and alignment of these cells, two parameters-directedness and orientation—are used with the following definition. See FIG. 7(a).

The directedness of cell electrotaxis is defined as the average of $$\cos \Phi = \Sigma_{i=1}^{n} \frac{\cos \Phi_i}{n},$$

where $\Phi_i$ is the angle between the Euclidean vector of each cell migration and the vector of applied EF (from anode to cathode), and n is the total number of analyzed cells (see FIG. 7(a)). A group of anodal moving cells holds a directedness of −1; and a group of cathodal moving cells holds a directedness of +1. For a group of randomly migrating cells, the directedness is zero.

The orientation is defined as the average of $$\cos 2\theta = \Sigma_{i=1}^{n} \frac{\cos 2\theta_i}{n},$$

where $\theta_i$ is the angle between the vector of applied EF and the long axis of a given cell; n is the total number of cells analyzed. A group of cells aligned perpendicular to the EF holds an orientation of −1; and a group of cells aligned in parallel to the applied EF holds an orientation of +1. For a group of randomly shaped cells, the average orientation is zero.

The directedness and orientation of the cells with and without EF stimulation, evaluated by the definitions pro-

TABLE 2

Stimulation area and effective stimulation percentage of in vitro EF stimulation devices

| Report | Substrate | Thickness (mm) | Stimulation area (cm²) | Total area (cm²) | Effective stimulation area percentage |
|---|---|---|---|---|---|
| Song et al. [NPL No. 27] | 100 mm TCPS | 0.13-0.16 | 2.2 | 55 | 4.0% |
| Song et al. [NPL No. 27] | 100 mm TCPS | 0.13-0.16 | 22 | 55 | 36.0% |
| Tandon et al. [NPL No. 52] | 60 mm glass | 0.25 | 6.5 | 21 | 30.9% |
| Babona-Pilipos et al. [NPL No. 53] | 60 mm TCPS | 0.17 | 2.2 | 21 | 10.5% |
| Huang et al. [NPL No. 29] | 150 mm TCPS | 0.07 | 19.2 | 152 | 12.6% |
| Tsai et al. [NPL No. 30] | 150 mm TCPS | 0.6 | 69 | 152 | 45.4% |
| This disclosure | 6-well TCPS 35 mm TCPS | 0.26 | 6.61 | 9.5 | 69.5% |
|  | 6-well TCPS 35 mm TCPS | 0.13 | 6.83 | 9.5 | 71.9% |
|  | 100 mm TCPS | 0.26 | 49 | 55 | 89.0% |
|  | 100 mm TCPS | 0.13 | 49.6 | 55 | 90.3% |

<Cell Migration and Alignment Under Uniform EF Stimulation>

NIH/3T3 fibroblast cells were used to further verify the performance of the inserts according to embodiments of the present invention because they are known to align perpendicular to the EF vector after stimulation and they have shown cathodal electrotaxis (NPL Nos. 49-51). The phase contrast microscopy images of the cells under 300 mV/mm EF stimulation over 5 hours were taken and analyzed. FIG. 8 shows the phase contrast microscopy images of NIH/3T3 vided above, are shown in FIG. 9. NIH/3T3 demonstrate strong cathodal electrotaxis under 300 mV/mm EF for 5 hours in both rectangular microfluidic chip and in the circular insert (p<0.0001, in comparison to their respective controls without EF stimulation) (FIG. 9(b)). While the directedness of NIH/3T3 cells in the polymer insert is slightly lower than that in the rectangular channels (0.78±0.02 v.s. 0.87±0.01), there was no statistical significance between the two (p>0.05). This deviation is possibly caused by un-optimized cell culture medium flow rate. While the shear stress in the polymer insert device and the rectangular channel is of the same order, the medium replenishment takes longer for the circular insert due to its bigger cross-sectional area.

Before EF stimulation, cells in both rectangular channels and circular inserts demonstrated random orientation (0.05 to 0.09). After 300 mV/mm EF stimulation, the orientation of cells in rectangular channels and circular insert decreased to −0.60±0.05 and −0.49±0.06, indicating perpendicular alignment (FIG. 9(c)). The difference of cell alignment in rectangular channels and circular inserts are significant before and after the stimulation (p<0.0001). The control cells in both rectangular channels and the circular inserts do not show any alignment.

Detailed cell migration and orientation data are shown in Table 3 below. These results validated the performance of the inserts according to embodiments of the present invention for electrotaxis experiments comparable to the performance of a rectangular channel. However, the circular inserts have at least two fold higher effective stimulation percentage in comparison to that of rectangular channels. Thus, a higher cell yield can be achieved by using our circular inserts of the present invention.

TABLE 3

Quantitative analysis of cells tracked in time-lapse electrotaxis experiments

| | N | directednes | SEM | orientation 0 hr | SEM | orientation 5 hr | SEM |
|---|---|---|---|---|---|---|---|
| 300 mV/mm rectangular | 106 | 0.8753 | 0.014 | −0.07 | 0.069 | −0.60 | 0.053 |
| 300 mV/mm circular insert | 110 | 0.7758 | 0.021 | −0.04 | 0.062 | −0.49 | 0.056 |
| Control rectangular channel | 118 | −0.03 | 0.059 | −0.05 | 0.067 | −0.07 | 0.062 |
| Control circular insert | 103 | 0.01 | 0.064 | −0.07 | 0.069 | −0.09 | 0.07 |

N: number of cells analyzed; SEM: standard error of mean.

In some embodiments of the present invention, a removable polymeric insert can further aid cell recovery right after the EF stimulation, which can be accomplished by adding a perfluoropolymer-coated layer between the adhesive tape and the insert (NPL No. 30). Alternatively, the removable insert can be fabricated by using polydimethyl-siloxane as the insert material. The silicone rubber can reversibly bond to the TCPS dish with air-tight seal by the clip-on design, similar to those in a transwell insert.

Additional Embodiments

Inserts for 15 mm diameter well with a 24-well plate were fabricated as embodiments of the present invention and tested. In this embodiment, based on the calculation and use of evaluation by commercially available software Mathematica, the following paraboloids parameters, $P_1$ were used to modify a 2.3 mm-high cylinder with a shell thickness of 0.1 mm. The bottom chamber thickness was set to 0.05 mm. The very thin bottom chamber enables high electric field strength with low electric current input:

$$P_1 : x^2 + y^2 = -\frac{z}{0.02653}$$

The small size of this 3D structured insert in 15 mm diameter cultureware allows the use of two-photon polymerization technique in manufacturing the insert. Thus, a smooth structure, instead of a layer-by-layer approximated multi-layered structure, can be fabricated, which is advantageous.

Due to the small configuration of 24-well dishes, the insert was designed to have minimized two interfaces, where salt bridges share the same interface with the inlet and outlet ports. This design also allows more space for easier and higher quality imaging.

In FIG. 10, (a) shows the improved model with the new interface design. In FIG. 10, (b) shows the electric field distribution simulated at the bottom of the insert of the new design, performed by COMSOL Multiphysics. The electric field coefficient of variation (CV) in the numerical simulation of 15 mm model is 1.47%, which is excellent.

Various embodiments described above are summarized in Table 4 below.

TABLE 4

Summary of completed and optimized designs for different sizes of cell cultureware

| Well size | 6-well (30 mm) | 6-well (30 mm) | 24-well (15 mm) | 100 mm | 100 mm |
|---|---|---|---|---|---|
| Height | 3.9 mm | 4.5 mm | 2.3 mm | 8 mm | 8 mm |
| Cylinder thickness | 0.5 mm | 0.25 mm | 0.1 mm | 0.5 mm | 0.25 mm |
| $b/a^2$ | −0.01047 | −0.01047 | −0.02653 | −0.00393 | −0.00393 |
| Chamber thickness | 0.26 mm | 0.13 mm | 0.05 mm | 0.26 mm | 0.13 mm |
| Number of interface | 4 | 4 | 2 | 4 | 4 |
| Cell culture area | 6.61 cm$^2$ | 6.83 cm$^2$ | 1.54 cm$^2$ | 49 cm$^2$ | 49.6 cm$^2$ |
| Effective stimulation area percentage | 69.5% | 71.9% | 81.1% | 89.0% | 90.3% |
| EPS CV (%) | 1.22% | 1.43% | 1.47% | 1.51% | 2.68% |

<Detailed Design Procedure>

In contrast to the conventional in vitro EF stimulation systems using a rectangular chamber, establishing a uniform EF in a circular shaped chamber (e.g., tissue culture polystyrene petri dish) is extremely difficult. This section describes the design principle for a 3D CAD insert of the type illustrated in FIG. 2(c), for example, in a microfluidic system, with the aim to create a uniform EF in the bottom chamber where cells are cultured and stimulated.

To maximize the cellular products for biochemical analysis, one desires to use as much of culture area as possible to increase the amount of cells to be stimulated in the circular chamber with a given height (the circular bottom channel shown in FIG. 2(a)). The electric field will be applied through a thin layer of fluid volume surrounding the perimeter of the bottom chamber through the insert, and the fluid volume can be treated as a thin liquid column (LC in FIG. 2(a)). However, a uniform EF cannot be created by applying two electric potentials on top of this liquid column (cylindrical side channel).

To create a uniform EF, the electrical resistance from one electrode to the other through any cross-section in the system must be the same. To address this challenge, a three dimensionally (3D) designed structure is devised to equalize the electrical resistances through any arbitrary current line that passes through the bottom circular chamber. Such structure can be approximated as the liquid column (LC) intersected by two identical circular paraboloids (P1 and P2) at the intersection of midpoint between the two potentials and the diameter of the liquid column (FIG. 2 (b)). The resulting 3D CAD structure to equalize the electrical resistance can be created by trimming the liquid column (i.e., the cylindrical side channel) using the circular paraboloids. Boolean difference tool was used in the CAD software to carry out this step. The 3D CAD model can then be used to create a uniform EF in the assembled microfluidic chip. According to Ohm's law, electrical resistance R can be described as follows (NPL No. 60):

[FORMULA 1]

$$R = \frac{l}{A_{cross\text{-}section}}, \tag{1}$$

where ρ is the resistivity, 1 is the length, and $A_{cross\text{-}section}$ is the cross-sectional area of the conductor. The arc length of the curves needs to be identified in this system to calculate the electrical resistance. Using a polar coordinate system, the bottom chamber (FIG. 2(a), the bottom circle) resides on the xy plane and the liquid column (the cylindrical sidewall part) on top possesses a diameter of $$\overline{BC}.$$

For paraboloid $P_1$, its apex resides with the origin 0 in the liquid column and the yz plane. The paraboloid intersects with the liquid column at the curve $$M' = \overline{AOD}$$

(white dashed line, FIG. 2(a)). The projections of points A and D on xy plane are B and C. Consider an electrical current owing from point A to point D. By Ohm's law, in order to have a uniform EF in the chamber bottom, the resistance of $$\overline{AOD}$$

(FIG. 2(a), the dashed path) must be equal to that of $$\overline{AB} + \overline{BC} + \overline{CD},$$

equivalently, $$R_{M'} = R_{\overline{AB}} + R_{\overline{BC}} + R_{\overline{CD}}.$$

If we assume the resistivity is the same across the sample, then the following is satisfied.

$$\frac{\overline{AOD}}{A_{M'}} = \frac{M'}{A_{M'}} = \frac{\overline{AB}}{A_{AB}} + \frac{\overline{BC}}{A_{BC}} + \frac{\overline{CD}}{A_{CD}}. \tag{2}$$

Equation 2 shows that a uniform EF distribution can be enabled when the ratio of the rectification of the curve M' over the cross-sectional area of the liquid column equals to the ratio of $$\overline{AB} + \overline{CD}$$

over the cross-sectional area of the liquid column, in addition to $$\overline{BC}$$

over the cross-sectional area of the bottom chamber. Assuming all electrical currents pass through sufficiently thin paths, then the following is satisfied.

$$\frac{M'}{\text{column thickness}} = \frac{2 \times \overline{AB}}{\text{column thickness}} + \frac{\overline{BC}}{\text{chamber depth}}. \tag{3}$$

Since $$\overline{AB}$$

and $$\overline{BC}$$

can be easily measured, the value of M' can be subsequently extracted by using Equation 3. With the information of M', the shape of the circular paraboloid $P_1$ and $P_2$ can be determined as follows.

The shape for the circular paraboloid P1 and P2 can be described as $$\frac{x^2 + y^2}{a^2} = \frac{z}{b}, \tag{4}$$

where $a^2/b$ is the constant describing the level of curvature in xz and yz planes of the paraboloid, which defines the shape of the paraboloid.

The equation for the liquid column can be considered as $$x^2 + (y-r)^2 = r^2, \tag{5}$$

where r is the radius of the column (also the radius of the circular bottom chamber). The coordinates of points O, A, and D can be presented in parametric form $$\left( r \cos \theta, r(1 - \sin \theta), \frac{2br^2}{a^2}(1 - \sin \theta) \right),$$

with

-continued $$O: \left( r\cos\frac{\pi}{2}, r\left(1-\sin\frac{\pi}{2}\right), \frac{2br^2}{a^2}\left(1-\sin\frac{\pi}{2}\right) \right) = (0, 0, 0), \quad (6a)$$

$$A: \left( r\cos 0, r(1-\sin 0), \frac{2br^2}{a^2}(1-\sin 0) \right) = \left( r, r, \frac{2br^2}{a^2} \right), \quad (6b)$$

$$D: \left( r\cos \pi, r(1-\sin \pi), \frac{2br^2}{a^2}(1-\sin \pi) \right) = \left( -r, r, \frac{2br^2}{a^2} \right), \quad (6c)$$

The rectification of curve M' along the paraboloid $P_1$ can be calculated by integrating parametric equations (NPL No. 61), $$M' = \int_0^\pi \sqrt{\left(\frac{dx}{d\theta}\right)^2 + \left(\frac{dy}{d\theta}\right)^2 + \left(\frac{dz}{d\theta}\right)^2}\, d\theta \quad (7a)$$

$$= \int_0^\pi \sqrt{(-r\sin\theta)^2 + (-r\cos\theta)^2 + \left(-\frac{2br^2}{a^2}\times\cos\theta\right)^2}\, d\theta \quad (7b)$$

$$= \int_0^\pi \sqrt{r^2 + \left(\frac{2br^2}{a^2}\right)^2 - \left(\frac{2br^2}{a^2}\right)^2 \sin^2\theta}\, d\theta. \quad (7c)$$

The constant of the paraboloid $$\frac{a^2}{b}$$

can be solved by solving Equation 3. Equation 3 is difficult to solve explicitly due to elliptic integral of the second kind related to M' along the paraboloid $P_1$ (Equation 7). But Equation 3 can be evaluated using Mathematica using the following code (Listing 1) by denoting a constant $$c = \frac{2br^2}{a^2}$$

(r is the radius of the circular bottom chamber) to simplify the calculation.

Listing 1: Example Code to Find the Descriptor for the Paraboloid P1:

```
Plot[Evaluate[Integrate[Sqrt[225+c^2-c^2*
    Sin [x]^2,{x,0,Pi}]/0.5-2*c/0.5-30/0.26],
    {c,-4.715,-4.71}]
```

To design an insert for 6-well plates, denote the thickness of the liquid column to be 0.5 mm, the diameter of the bottom chamber to be 30 mm, and the thickness of the bottom chamber to be 0.26 mm, the parameter $$c = \frac{2br^2}{a^2}$$

(containing the constant for the paraboloid $P_1$) can be evaluated and used to create the 3D model (described below) in a commercial CAD software for further numerical simulation and device fabrications.

$$\frac{b}{a^2} = -0.01047. \quad (8)$$

$$P_1: x^2 + y^2 = -\frac{z}{0.01047}. \quad (9)$$

With this design principle, two extreme cases can be considered: electrical current passing through the shortest chord and the longest chord (i.e., diameter), which will yield the constant of the paraboloid and the height of the liquid column required to achieve uniform EF. To find the electrical resistance for all arbitrary current lines passing through each different paths (for example, path line curves M'', M**, M*, and M' in FIG. 2(a)) between the shortest chord ($\theta$=90), where $\theta$ is the polar coordinate azimuth, the following equation in listing 2 can be used.

Listing 2: Examples Code for all M Paths:

```
Table[Evaluate[2*Integrate[Sqrt[225+4.713^2-
    4.713^2*Sin [x]^2],{x,0,y}]/0.5+2*(-4.713)*(1-
    Sin [y])/0.5+2*15*Sin [Pi/2-y]/0.26],{y,0,Pi/2,
    Pi/180}]
```

The calculated resistance range with $$\theta \in (0°, 90°)$$

is plotted in FIG. 11. The relative resistance of $$\overline{AB} + \overline{BC} + \overline{CD}$$

corresponds to $\theta$=0 and that of $$\overline{AOD}$$

corresponding to $\theta$=90. The results show that resistances of all path lines converge toward both extreme cases, and this model provides a good approximation to achieve uniform EF in a circular chamber. Quadratic surface integral should also be helpful to further improve this design procedure.

In sum, establishment of a uniform EF in a circular-shaped microdevice is extremely difficult so the majority of existing EF stimulation devices avoids this issue by using a simple rectangular shaped chamber. The rectangular configuration requires modification to fit with the commercial labware, and only a small portion of the cell culture dish is used for cell culture, thus limiting the cell yield. By adding a 3D CAD based insert according to embodiments of the present invention in a circular shaped cell culture chamber, the present disclosure demonstrated that a uniform EF can be created in a circular-shaped area by modulating the electrical resistance across the device.

In some aspects of the present invention, the following features can be noted, some of which have been described above.

(1) The effective stimulation area percentage using the insert is at least 2 fold higher than that of existing EF stimulation devices. The yield of cells and its products can be increased for further biochemical analysis.

(2) The same CAD design principle can be easily scaled up or down to tailor design inserts for different sized TCPS dishes. Mass production of the polymeric insert can be achieved by CNC fabrication, injection molding, or other similar technology. The polymeric insert is useful for adapting electrical stimulation studies in a common laboratory due to the high effective stimulation area percentage and the ease of use.

(3) The polymeric insert is applicable for various studies. For tissue engineering, EF stimulation has been reported to induce synchronously contracting cardiac tissue (NPL Nos.

52 and 54-57). Osteoblastic differentiation from mesenchymal stem cells can be promoted under EF stimulation (NPL No. 58). Uniform EF stimulation to circular shaped area could also be useful to stimulate an entire brain slice or tissue slice.

It will be apparent to those skilled in the art that various modification and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

The invention claimed is:

1. An insert configured to be inserted into a circular-shaped petri dish for generating a substantially uniform electric field across the petri dish, when the petri dish is filled with a fluid, to establish a salt bridge, the insert comprising:
    a circular-shaped bottom plate configured to be fitted into the circular-shaped petri dish, the bottom plate defining a circular-shaped space of a substantially uniform thickness together with a circular-shaped bottom surface of the petri dish as a channel accepting said fluid when the insert is inserted into the petri dish;
    a side channel vertically erecting from a circular periphery of said bottom plate, the side channel communicating with said circular shaped space defined by the bottom plate so as to accept said fluid; and
    a pair of current rectifying chambers each having a generally planar shape connecting to and communicating with the side channel, the current rectifying chambers being diagonally disposed to face each other along a diameter of the circular shaped bottom plate and being line-symmetric with each other with respect to said diameter, each of the current rectifying chambers extending inwardly from a respective portion of a top end of the side channel and having a salt bridge port to accept the fluid and provide the fluid to said circular-shaped space defined by the bottom plate through said side channel so as to establish the salt bridge,
    wherein portions of the side channel other than the portions thereof respectively connecting to the current rectifying chambers each have a generally concave top profile having a lowest point at a center between the pair of current rectifying chambers and are each shaped such that when the salt bridge is established, the circular-shaped space defined by the bottom plate exhibits a substantially uniform electric field in a direction of said diameter in a substantially entire area thereof.

2. The insert according to claim 1, wherein the circular shaped petri dish is a tissue-culture polystyrene (TCPS) petri dish.

3. The insert according to claim 1, wherein said generally concave top profile of the side channel outlines a curve defined by an intersection of a paraboloid with a cylindrical column.

4. The insert according to claim 3, wherein said generally concave top profile of the side channel has a stair-like shape outlining said curve.

5. A device for establishing a uniform electric field in a circular-shaped space filled with a fluid having a prescribed resistivity, the device comprising a unitary or multipart member that: comprises the circular-shaped petri dish and the insert according to claim 1.

* * * * *